US 6,749,978 B2

(12) United States Patent
Jubran et al.

(10) Patent No.: US 6,749,978 B2
(45) Date of Patent: Jun. 15, 2004

(54) ELECTROPHOTOGRAPHIC ORGANOPHOTORECEPTORS WITH NOVEL CHARGE TRANSPORT COMPOUNDS

(75) Inventors: Nusrallah Jubran, St. Paul, MN (US); Zbigniew Tokarski, Woodbury, MN (US); Kam Law, Woodbury, MN (US); Vytautas Getautis, Kaunas (LT); Jonas Sidaravicius, Vilnius (LT); Osvaldas Paliulis, Kaunas (LT); Valentas Gaidelis, Vilnius (LT); Vygintas Jankauskas, Vilnius (LT)

(73) Assignee: Samsung Electronics Co., Ltd., Kyungki-Do (KR)

( * ) Notice: Subject to any disclaimer, the term of this patent is extended or adjusted under 35 U.S.C. 154(b) by 0 days.

(21) Appl. No.: 10/449,554

(22) Filed: May 30, 2003

(65) Prior Publication Data

US 2003/0219662 A1 Nov. 27, 2003

Related U.S. Application Data

(63) Continuation-in-part of application No. 09/963,141, filed on Sep. 24, 2001, now Pat. No. 6,670,085.

(51) Int. Cl.$^7$ .............................................. G03G 15/02
(52) U.S. Cl. ...................... 430/58.6; 430/58.4; 548/416
(58) Field of Search ............................... 430/58.6, 58.4; 548/416

(56) References Cited

U.S. PATENT DOCUMENTS

| | | | |
|---|---|---|---|
| 4,297,426 A | 10/1981 | Sakai et al. .................... | 430/59 |
| 4,786,571 A | 11/1988 | Ueda ............................. | 430/59 |
| 4,931,371 A | 6/1990 | Matsumoto et al. .......... | 430/59 |
| 4,957,838 A | 9/1990 | Aruga et al. ................... | 430/59 |
| 5,128,227 A | 7/1992 | Monbaliu et al. ............. | 430/59 |
| 5,604,065 A | 2/1997 | Shimada et al. .............. | 430/83 |
| 5,747,203 A | 5/1998 | Nozomi et al. ................ | 430/58 |
| 5,932,384 A | 8/1999 | Mitsumori et al. ........... | 430/59 |
| 6,001,522 A | 12/1999 | Woo et al. ...................... | 430/65 |
| 6,020,096 A | 2/2000 | Fuller et al. ............... | 430/58.35 |
| 6,030,734 A | 2/2000 | Mitsumori ................ | 430/58.8 |
| 6,040,098 A | 3/2000 | Black et al. ................ | 430/59.6 |
| 6,066,426 A | 5/2000 | Mott et al. .................. | 430/58.2 |
| 6,066,427 A | 5/2000 | Black et al. ................ | 430/58.4 |
| 6,099,996 A | 8/2000 | Yanus et al. ................ | 430/58.8 |
| 6,099,997 A | 8/2000 | Terrell et al. .............. | 430/59.1 |
| 6,106,989 A | 8/2000 | Bretscher et al. ........... | 430/132 |
| 6,140,004 A | 10/2000 | Mott et al. .................. | 430/132 |
| 6,214,503 B1 | 4/2001 | Gaidelis et al. ........... | 430/58.45 |

FOREIGN PATENT DOCUMENTS

WO    WO 01/46757 A1    6/2001    ............. G03G/5/06

OTHER PUBLICATIONS

Chemical Abstracts, Columbus, OH, US vol. 101, No. 17, Sep. 17, 1984, XP–002233044, XP–002233046 & JP 58 091457 A.

Chemical Abstracts, Columbus, OH US vol. 119, No. 10, Sep. 6, 1993, XP–002233045 & JP 05 100456 A.

Primary Examiner—Mark A. Chapman
(74) Attorney, Agent, or Firm—Patterson, Thuente, Skaar & Christensen, P.A.

(57) ABSTRACT

Charge transport compounds are described that have a multiple number of hydrazone-bridged heterocyclic groups (especially julolidine groups, carbazole groups, triarylamine groups and (N,N-disubstituted)arylamine groups such as dialkarylamine groups (e.g. dimethylphenylamine; methylethylphenylamine, dipropylphenylamine, ethylepropylphenylamine, ethylbutylnaphthylamine, etc.), alkyldiarylamine groups (e.g. methyldiphenylamino, ethyldiphenylamino, etc), and triarylamino groups (e.g., triphenyl amino, trinaphthylamino, etc)) connected by a central bridging group. An example of charge transport compounds are those having the following generic formula:

$$(R-Q)n-Y \qquad \text{Formula I}$$

wherein R is selected from the group consisting of julolidine ring groups, carbazole ring groups, and and (N,N-disubstituted)arylamine groups;

Q comprises an aromatic hydrazone linking group, such as

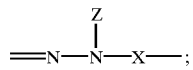

Y comprises a bridging group between R—Q— groups, such as a bond, carbon atom, nitrogen atom, oxygen atom, sulfur atom, a methylene group; Z is an aryl group, preferably a phenyl group or naphthyl group; X is a linking group, preferably a methylene group, and for example having the formula —$(CH_2)_m$— (branched or linear), where m is an integer between 0 and 20, inclusive, and one or more of the methylene groups is optionally replaced by an oxygen atom, a carbonyl group, urethane, urea, an ester group, a —$NR_6$ group, a $CHR_7$ group, or a $CR_8R_9$ group where $R_6$, $R_7$, $R_8$, and $R_9$ are, independently, H, an alkyl group, or aryl group; and n is an integer between 2 and 6, inclusive. An organic photoreceptor includes that compound and (b) a charge generating compound; and (c) an electrically conductive substrate.

22 Claims, No Drawings

ELECTROPHOTOGRAPHIC ORGANOPHOTORECEPTORS WITH NOVEL CHARGE TRANSPORT COMPOUNDS

RELATED APPLICATIONS

This application is a continuation-in-part of U.S. patent application Ser. No. 09/963,141 filed on Sep. 24, 2001 now U.S. Pat. No. 6,670,085 titled "ELECTROPHOTOGRAPHIC ORGANOPHOTORECEPTORS WITH NOVEL CHARGE TRANSPORT COMPOUNDS."

BACKGROUND OF THE INVENTION

1. Field of the Invention

This invention relates to organophotoreceptors suitable for use in electrophotography and, more specifically, to organophotoreceptors having novel charge transport compounds.

2. Background of the Art

In electrophotography, an organophotoreceptor in the form of a plate, disk, sheet, belt, or drum having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and uncharged areas. A liquid or solid toner is then deposited in either the charged or uncharged areas to create a toned image on the surface of the photoconductive layer. The resulting visible toner image can be transferred to a suitable receiving surface such as paper. The imaging process can be repeated many times.

Both single layer and multilayer photoconductive elements have been used. In the single layer embodiment, a charge transport material and charge generating material are combined with a polymeric binder and then deposited on the electrically conductive substrate. In the multilayer embodiment, the charge transport material and charge generating material are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and electrons) upon exposure to light. The purpose of the charge transport material is to accept these charge carriers and transport them through the charge transport layer in order to discharge a surface charge on the photoconductive element.

To produce high quality images, particularly after multiple cycles, it is desirable for the charge transport material to form a homogeneous solution with the polymeric binder and remain in solution. In addition, it is desirable to maximize the amount of charge which the charge transport material can accept (indicated by a parameter known as the acceptance voltage or "$V_{acc}$"), and to minimize retention of that charge upon discharge (indicated by a parameter known as the discharge voltage or "$V_{dis}$").

There are many charge transport materials available for electrophotography. The most common charge transport materials are pyrazoline derivatives, fluorene derivatives, oxadiazole derivatives, stilbene derivatives, hydrazone derivatives, carbazole hydrazone derivatives, polyvinyl carbazole, polyvinyl pyrene, or polyacenaphthylene. However, each of the above charge transport materials suffers some disadvantages. There is always a need for novel charge transport materials to meet the various requirements of electrophotography applications.

SUMMARY OF THE INVENTION

A charge transport compound having the following generic formula:

(R—Q)n-Y                      Formula I wherein R is a heterocyclic group, preferably a heterocyclic group selected from the group consisting of julolidine ring groups, carbazole ring groups, and (N,N-disubstituted) arylamine groups such as dialkarylamine groups (e.g. dimethylphenylamine; methylethylphenylamine, dipropylphenylamine, ethylepropylphenylamine, ethylbutylnaphthylamine, etc.), alkyldiarylamine groups (e.g. methyldiphenylamino, ethyldiphenylamino, etc), and triarylamino groups (e.g., triphenyl amino, trinaphthylamino, etc), wherein it is preferred that at least one of the n R groups comprises (N,N-disubstituted) arylamine groups such as dialkarylamine groups, alkyldiarylamine groups, etc), and triarylamino groups;

Q comprises an aromatic hydrazone linking group, such as

Y comprises a bridging group between R—Q— groups, such as a bond, carbon atom, nitrogen atom, oxygen atom, sulfur atom, a branched or linear —(CH$_2$)$_p$— group where p is an integer between 0 and 10, an aryl group, a cycloalkyl group, a cyclosiloxyl group (e.g., a cyclotetrasiloxyl group), a heterocyclic group, or a CR$_{10}$ group where R$_{10}$ is hydrogen atom, an alkyl group, or aryl group;

Z is an aryl group, preferably a phenyl group or naphthyl group;

X is a linking group, preferably a methylene group, and for example having the formula —(CH$_2$)$_m$— (branched or linear), where m is an integer between 0 and 20, inclusive, and one or more of the methylene groups is optionally replaced by an oxygen atom, a carbonyl group, urethane, urea, an ester group, a —NR$_6$ group, a CHR$_7$ group, or a CR$_8$R$_9$ group where R$_6$, R$_7$, R$_8$, and R$_9$ are, independently, H, an alkyl group, or aryl group; and n is an integer between 2 and 6, inclusive.

In another aspect of the invention, the invention features an organic photoreceptor that includes:

(a) a charge transport compound having the formula (R—Q)n-Y                      Formula I wherein R is a heterocyclic group, preferably a heterocyclic group selected from the group consisting of julolidine ring groups, carbazole ring groups, and (N,N-disubstituted) arylamine groups such as dialkarylamine groups (e.g. dimethylphenylamine; methylethylphenylamine, dipropylphenylamine, ethylepropylphenylamine, ethylbutylnaphthylamine, etc.), alkyldiarylamine groups (e.g. methyldiphenylamino, ethyldiphenylamino, etc), and triarylamino groups (e.g., triphenyl amino, trinaphthylamino, etc) wherein it is preferred that at least one of the n R groups comprises (N,N-disubstituted) arylamine groups such as dialkarylamine groups, alkyldiarylamine groups, etc), and triarylamino groups;

Q comprises an aromatic hydrazone linking group, such as

Y comprises a bridging group, preferably a divalent linking group, between R—Q— groups, such as a bond, carbon atom, nitrogen atom, oxygen atom, sulfur atom, a branched or linear —(CH$_2$)$_p$— group where p is an integer between 0 and 10, an aryl group, a cycloalkyl group, a cyclosiloxyl group (e.g., a cyclotetrasiloxyl group), a heterocyclic group, or a CR$_{10}$ group where R$_{10}$ is hydrogen atom, an alkyl group, or aryl group;

Z is an aryl group, preferably a phenyl group or naphthyl group;

X is a linking group, preferably a methylene group, and for example having the formula —(CH$_2$)$_m$— (branched or linear), where m is an integer between 0 and 20, inclusive, and one or more of the methylene groups is optionally replaced by an oxygen atom, a carbonyl group, urethane, urea, an ester group, a —NR$_6$ group, a CHR$_7$ group, or a CR$_8$R$_9$ group where R$_6$, R$_7$, R$_8$, and R$_9$ are, independently, H, an alkyl group, or aryl group; and n is an integer between 2 and 6, inclusive;

(b) a charge generating compound; and (c) an electrically conductive substrate.

DETAILED DESCRIPTION OF THE INVENTION

A charge transport compound having the following generic formula:

(R—Q)n-Y    Formula I wherein R is a heterocyclic group, preferably a heterocyclic group selected from the group consisting of julolidine ring groups, carbazole ring groups, and (N,N-disubstituted) arylamine groups such as dialkarylamine groups (e.g. dimethylphenylamine; methylethylphenylamine, dipropylphenylamine, ethylepropylphenylamine, ethylbutylnaphthylamine, etc.), alkyldiarylamine groups (e.g. methyldiphenylamino, ethyldiphenylamino, etc), and triarylamino groups (e.g., triphenyl amino, trinaphthylamino, etc) wherein it is preferred that at least one of the n R groups comprises (N,N-disubstituted) arylamine groups such as dialkarylamine groups, alkyldiarylamine groups, etc), and triarylamino groups (and 1, 2, 3, 4, 5 or 6 R groups may be selected from these preferred classes);

Q comprises an aromatic hydrazone linking group, such as

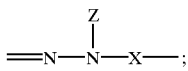

preferably Q comprises C(R')=N—N(Z)—X; with this definition available for all disclosed Q groups in all formulae of this disclosure, and R' may be hydrogen, alkyl groups, aryl groups, and alkaryl groups;

Y comprises a bridging group between R—Q— groups, such as a bond, carbon atom, nitrogen atom, oxygen atom, sulfur atom, a branched or linear —(CH$_2$)$_p$— group where p is an integer between 0 and 10, an aryl group, a cycloalkyl group, a cyclosiloxyl group (e.g., a cyclotetrasiloxyl group), a heterocyclic group, or a CR$_{10}$ group where R$_{10}$ is hydrogen atom, an alkyl group, or aryl group;

Z is an aryl group, preferably a phenyl group or naphthyl group;

X is a linking group, preferably a methylene group, and for example having the formula —(CH$_2$)$_m$— (branched or linear), where m is an integer between 0 and 20, inclusive, and one or more of the methylene groups is optionally replaced by an oxygen atom, a carbonyl group, urethane, urea, an ester group, a —NR$_6$ group, a CHR$_7$ group, or a CR$_8$R$_9$ group where R$_6$, R$_7$, R$_8$, and R$_9$ are, independently, H, an alkyl group, or aryl group; and n is an integer between 2 and 6, inclusive.

Various specific classes of charge transport compound within the scope of Formula I include, but are not limited to the following:

In a first aspect, the invention features an organophotoreceptor that includes:

(a) a charge transport compound having the formula

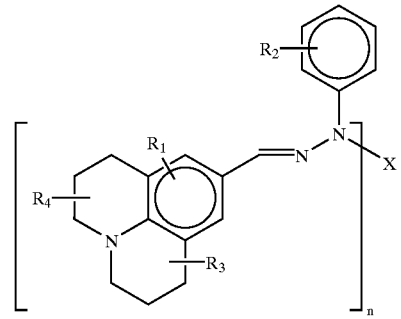

(II)

where n is an integer between 2 and 6, inclusive;

R$_1$, R$_2$, R$_3$, and R$_4$ are, independently, hydrogen, a halogen atom, hydroxy group, thiol group, an alkoxy group, a branched or linear alkyl group (e.g., a C$_1$–C$_{20}$ alkyl group), a branched or linear unsaturated hydrocarbon group, an ether group, nitro group, an amino group, a cycloalkyl group (e.g. a cyclohexyl group), or an aryl group (e.g., a phenyl or naphthyl group); and X is a linking group having the formula —(CH$_2$)$_m$—, branched or linear, where m is an integer between 0 and 50, inclusive, and one or more of the methylene groups is optionally replaced by a bond, an oxygen atom, a sulfur atom, a carbonyl group, an urethane group, an urea group, an ester group, an aryl group, a cycloalkyl group, a cyclosiloxyl group (e.g., a cyclotetrasiloxyl group), a heterocyclic group, a NR$_5$ group, a CHR$_6$ group, or a CR$_7$R$_8$ group where R$_5$, R$_6$, R$_7$, and R$_8$ are, independently, H, an alkyl group, or an aryl group.

The charge transport compound may or may not be symmetrical. Thus, for example, a linking group X for any given "arm" of the compound may be the same or different from the linking groups in other "arms" of the compound. Similarly, the R$_1$, R$_2$, R$_3$, and R$_4$ groups for any given "arm"

of the compound may be the same or different from the $R_1$, $R_2$, $R_3$, and $R_4$ groups in any other arm. In addition, the above-described formula for the charge transport compound is intended to cover isomers; or b) a charge transport compound of the formula:

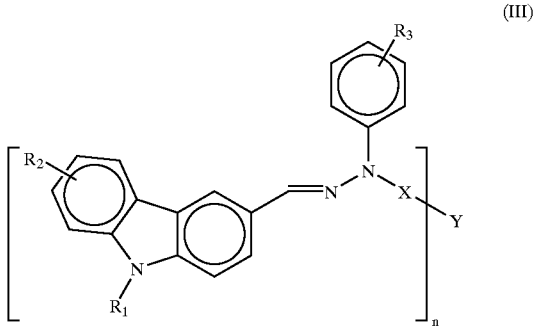

where n is an integer between 2 and 6, inclusive;

$R_1$ is hydrogen, a branched or linear alkyl group (e.g., a $C_1$–$C_{20}$ alkyl group), a branched or linear unsaturated hydrocarbon group, an ether group, or an aryl group (e.g., a phenyl or naphthyl group);

$R_2$ is hydrogen, a halogen, hydroxy group, thiol group, an alkoxy group, a branched or linear alkyl group (e.g., a $C_1$–$C_{20}$ alkyl group), a branched or linear unsaturated hydrocarbon group, an ether group, a cycloalkyl group (e.g. a cyclohexyl group), an aryl group (e.g., a phenyl or naphthyl group), or a —$NR_4R_5$ group where $R_4$ and $R_5$ are, independently, hydrogen, a branched or linear alkyl group, a branched or linear unsaturated hydrocarbon group, a cycloalkyl group, an aryl group, or $R_4$ and $R_5$ combine with the nitrogen atom to form a ring;

$R_3$ is hydrogen, a halogen, hydroxy group, thiol group, an alkoxy group, a branched or linear alkyl group (e.g., a $C_1$–$C_{20}$ alkyl group), a branched or linear unsaturated hydrocarbon group, an ether group, a cycloalkyl group (e.g. a cyclohexyl group), or an aryl group (e.g., a phenyl or naphthyl group);

X is a linking group having the formula —$(CH_2)_m$—, branched or linear, where m is an integer between 0 and 20, inclusive, and one or more of the methylene groups is optionally replaced by an oxygen atom, a carbonyl group, urethane, urea, an ester group, a —$NR_6$ group, a $CHR_7$ group, or a $CR_8R_9$ group where $R_6$, $R_7$, $R_8$, and $R_9$ are, independently, H, an alkyl group, or aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group (e.g., a cyclotetrasiloxyl group), a heterocyclic group, or a $CR_{10}$ group where $R_{10}$ is hydrogen atom, an alkyl group, or aryl group;

(b) a charge generating compound; and (c) an electrically conductive substrate.

The charge transport compound may or may not be symmetrical. Thus, for example, a linking group X for any given "arm" of the compound may be the same or different from the linking groups in other "arms" of the compound. Similarly, the $R_1$, $R_2$, and $R_3$ groups for any given "arm" of the compound may be the same or different from the $R_1$, $R_2$, and $R_3$ groups in any other arm. In addition, the above-described formula for the charge transport compound is intended to cover isomers.

The organic photoreceptor may be provided in the form of a flexible belt or rigid drum. In one embodiment, the organic photoreceptor includes: (a) a charge transport layer comprising the charge transport compound and a polymeric binder; (b) a charge generating layer comprising the charge generating compound and a polymeric binder; and (c) the electrically conductive substrate. The charge transport layer may be intermediate the charge generating layer and the electrically conductive substrate. Alternatively, the charge generating layer may be intermediate the charge transport layer and the electrically conductive substrate.

The invention also features the charge transport compounds themselves. In one preferred embodiment, a charge transport compound is selected in which n is 2, Y is a bond or a —$CH_2$— group, X has the formula —$(CH_2)_m$— where m is an integer between 2 and 5, inclusive, and $R_1$ is an ethyl, heptyl, or —$(CH_2)_3C_6H_5$ group. Specific examples of suitable charge transport compounds have the following formulae:

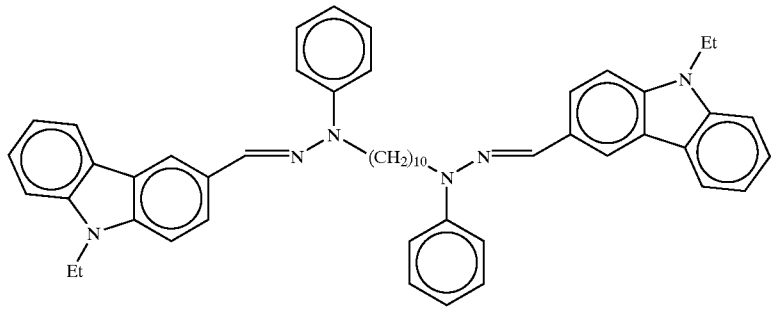

-continued
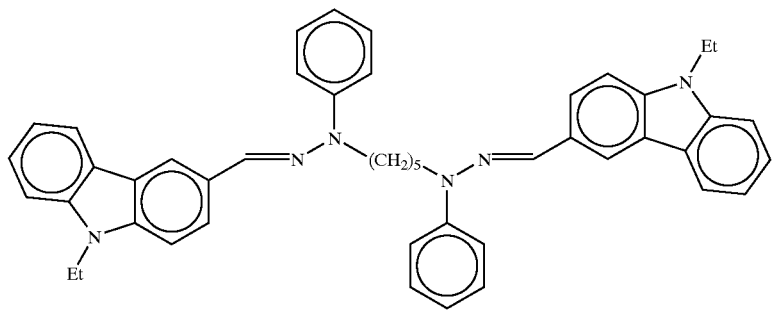
(2)
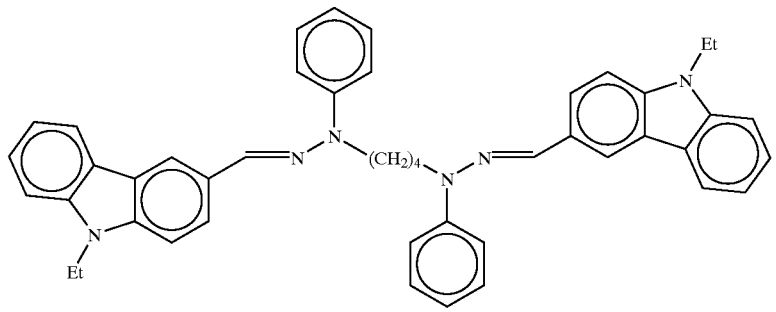
(3)
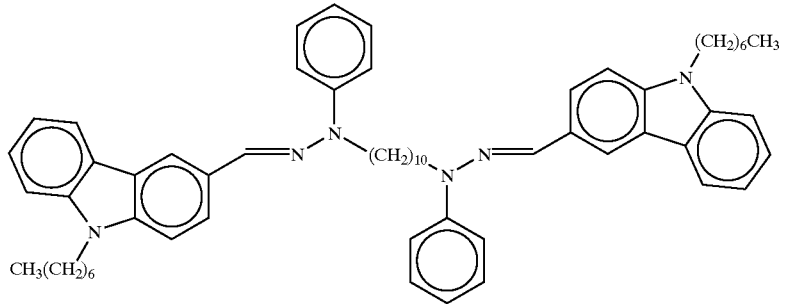
(4)
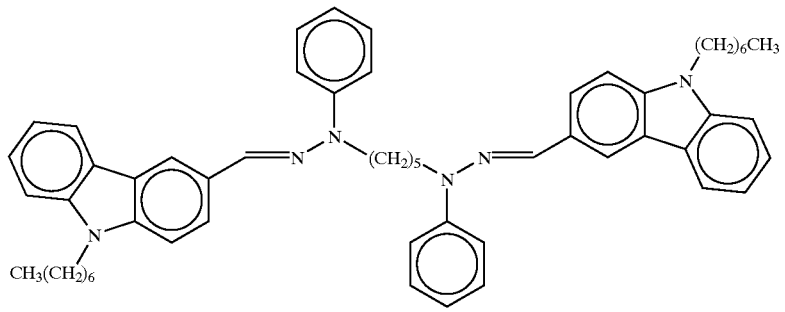
(5)
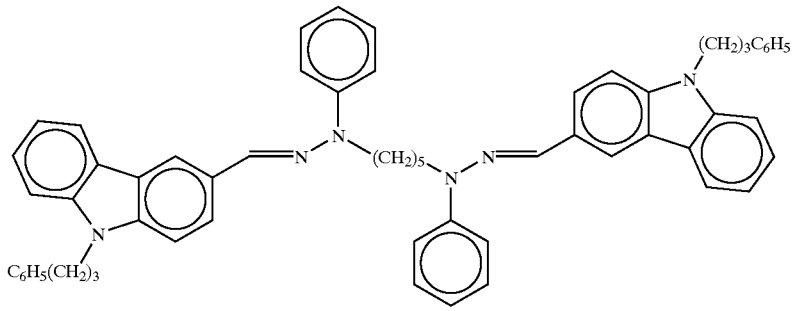
(6)

In one preferred embodiment, a charge transport compound is selected in which n is 2, X is a $(CH_2)_m$ group where m is an integer between 2 and 20, and $R_1$, $R_2$, $R_3$, and $R_4$ are hydrogen. Specific examples of suitable charge transport compound have the following general formula where m is an integer between 2 and 20;. more preferably m is an integer between 4 and 10; most preferably m is 5, as in Compound (11).

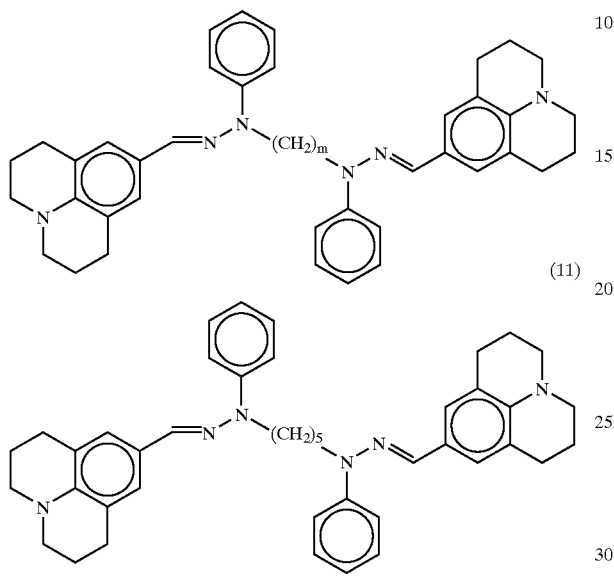

In a second aspect, the invention features an electrophotographic imaging apparatus that includes (a) a plurality of support rollers, at least one having a diameter no greater than about 40 mm; and (b) the above-described organic photoreceptor in the form of a flexible belt threaded around the support rollers. The apparatus preferably further includes a liquid toner dispenser.

In a third aspect, the invention features an electrophotographic imaging process that includes (a) applying an electrical charge to a surface of the above-described organic photoreceptor; (b) imagewise exposing the surface of the organic photoreceptor to radiation to dissipate charge in selected areas and thereby form a pattern of charged and uncharged areas on the surface; (c) contacting the surface with a liquid toner that includes a dispersion of colorant particles in an organic liquid to create a toned image; and (d) transferring the toned image to a substrate.

In a fourth aspect, the invention features a novel charge transport material having the formula (IV)

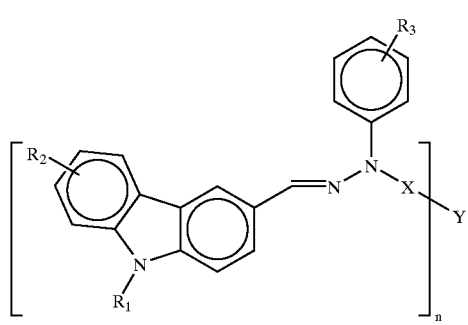

where n is an integer between 2 and 6, inclusive;

$R_1$ is hydrogen, a branched or linear alkyl group (e.g., a $C_1$–$C_{20}$ alkyl group), a branched or linear unsaturated hydrocarbon group, an ether group, or an aryl group (e.g., a phenyl or naphthyl group);

$R_2$ is hydrogen, a halogen, hydroxy group, thiol group, an alkoxy group, a branched or linear alkyl group (e.g., a $C_1$–$C_{20}$ alkyl group), a branched or linear unsaturated hydrocarbon group, an ether group, a cycloalkyl group (e.g. a cyclohexyl group), an aryl group (e.g., a phenyl or naphthyl group), or a —$NR_4R_5$ group where $R_4$ and $R_5$ are, independently, hydrogen, a branched or linear alkyl group, a branched or linear unsaturated hydrocarbon group, a cycloalkyl group, an aryl group, or $R_4$ and $R_5$ combine with the nitrogen atom to form a ring;

$R_3$ is hydrogen, a halogen, hydroxy group, thiol group, an alkoxy group, a branched or linear alkyl group (e.g., a $C_1$–$C_{20}$ alkyl group), a branched or linear unsaturated hydrocarbon group, an ether group, a cycloalkyl group (e.g. a cyclohexyl group), or an aryl group (e.g., a phenyl or naphthyl group);

X is a linking group having the formula —$(CH_2)_m$—, branched or linear, where m is an integer between 0 and 20, inclusive, and one or more of the methylene groups is optionally replaced by an oxygen atom, a carbonyl group, urethane, urea, an ester group, a —$NR_6$ group, a $CHR_7$ group, or a $CR_8R_9$ group where $R_6$, $R_7$, $R_8$, and $R_9$ are, independently, H, an alkyl group, or aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group (e.g., a cyclotetrasiloxyl group), a heterocyclic group, or a $CR_{10}$ group where $R_{10}$ is hydrogen atom, an alkyl group, or aryl group.

Mixed (e.g., at least two R groups are selected from two different classes selected from the group consisting of julolidine, carbazole, and triarylmethane) may be represented by the following various subgeneric formulae:

(V)

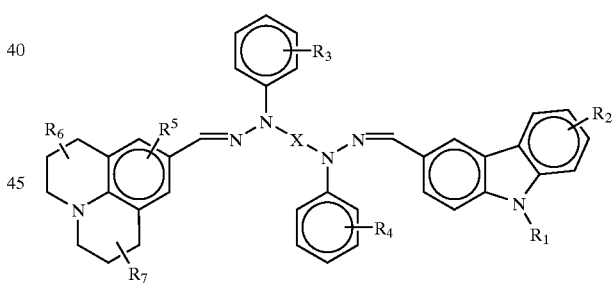

Specific subgeneric examples of charge transport compound according to Formula (V) have the following general Formula (VI) where m is an integer between 2 and 20; more preferably m is an integer between 4 and 10.

(VI)

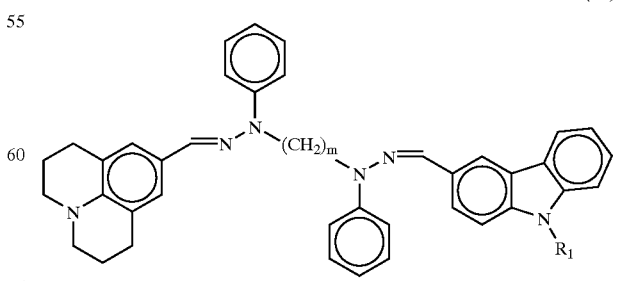

Another example of such a mixed charge transport compound has the formula (VI):

(VII)

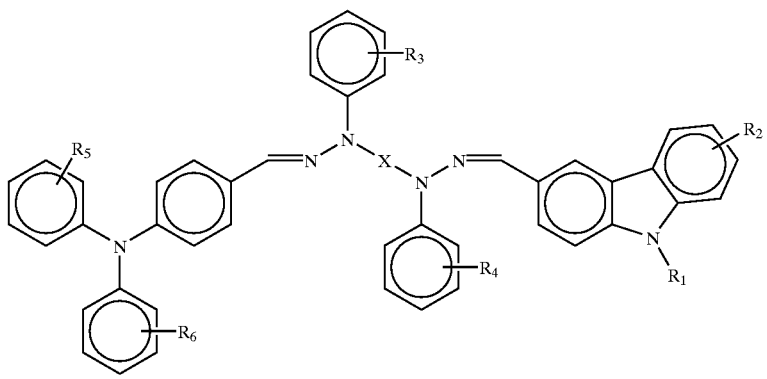

where $R_1$ is hydrogen, a branched or linear alkyl group (e.g., a $C_1$–$C_{20}$ alkyl group), a branched or linear unsaturated hydrocarbon group, a cycloalkyl group (e.g. a cyclohexyl group), or an aryl group (e.g., a phenyl or naphthyl group);

$R_2$, $R_3$, $R_4$, $R_5$, and $R_6$ are, independently, hydrogen, a halogen atom, hydroxy group, thiol group, an alkoxy group, a branched or linear alkyl group (e.g., a $C_1$–$C_{20}$ alkyl group), a branched or linear unsaturated hydrocarbon group, an ether group, nitro group, an amino group, a cycloalkyl group (e.g. a cyclohexyl group), or an aryl group (e.g., a phenyl or naphthyl group); and X is a linking group having the formula —$(CH_2)_m$—, branched or linear, where m is an integer between 0 and 50, inclusive, and one or more of the methylene ($CH_2$) groups is optionally replaced by oxygen atom, sulfur atom, a carbonyl group, an urethane group, an urea group, an ester group, an aryl group, a heterocyclic group, a cycloalkyl group, a cyclosiloxyl group (e.g., a cyclotetrasiloxyl group), a cycloalkyl group, a cyclosiloxyl group (e.g., a cyclotetrasiloxyl group), a $NR_7$ group, a $CHR_8$ group, or a $CR_9R_{10}$ group where $R_7$, $R_8$, $R_9$, and $R_{10}$, are, independently, H, an alkyl group, or an aryl group.

In one specific embodiment of structural Formula VII, a charge transport compound is selected in which X is a —$(CH_2)_m$— group where m is an integer between 2 and 20, $R_1$ is an alkyl group, and $R_2$, $R_3$, $R_4$, $R_5$ and $R_6$ are hydrogen. Specific examples of suitable charge transport compound have the following general formula where m is an integer between 2 and 20; more preferably m is an integer between 4 and 10.

(VIII)

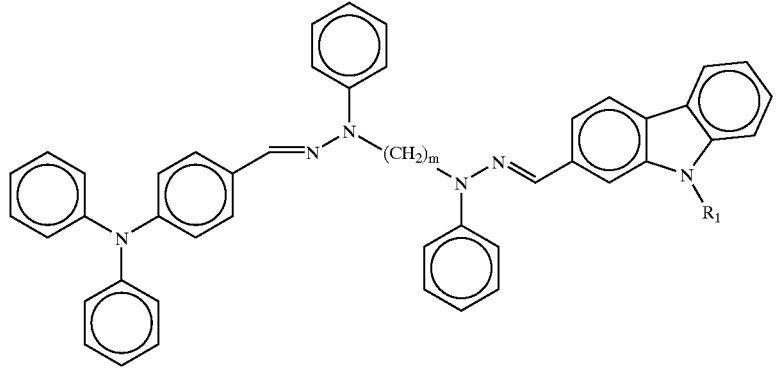

and Formula (IX) wherein:
the subgeneric formula below applies:

(IX)

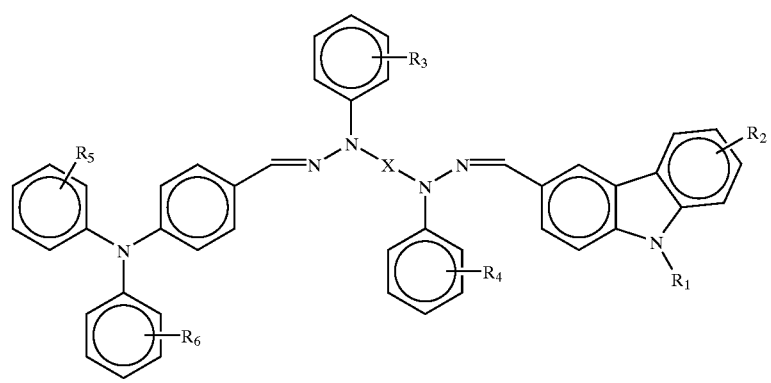

where $R_1$ is hydrogen, a branched or linear alkyl group (e.g., a $C_1$–$C_{20}$ alkyl group), a branched or linear unsaturated hydrocarbon group, a cycloalkyl group (e.g. a cyclohexyl group), or an aryl group (e.g., a phenyl or naphthyl group);

$R_2$, $R_3$, $R_4$, $R_5$, and $R_6$ are, independently, hydrogen, a halogen atom, hydroxy group, thiol group, an alkoxy group, a branched or linear alkyl group (e.g., a $C_1$–$C_{20}$ alkyl group), a branched or linear unsaturated hydrocarbon group, an ether group, nitro group, an amino group, a cycloalkyl group (e.g. a cyclohexyl group), or an aryl group (e.g., a phenyl or naphthyl group); and X is a linking group having the formula —$(CH_2)_m$—, branched or linear, where m is an integer between 0 and 50, inclusive, and one or more of the methylene ($CH_2$) groups is optionally replaced by oxygen atom, sulfur atom, a carbonyl group, an urethane group, an urea group, an ester group, an aryl group, a heterocyclic group, a cycloalkyl group, a cyclosiloxyl group (e.g., a cyclotetrasiloxyl group), a $NR_7$ group, a $CHR_8$ group, or a $CR_9R_{10}$ group where $R_7$, $R_8$, $R_9$, and $R_{10}$, are, independently, H, an alkyl group, or an aryl group.

Another generic Formula (IX) is directed to charge transport compounds having the formula

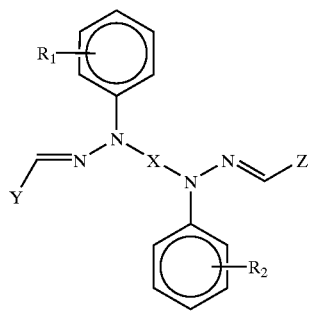

(X)

wherein $R_1$ and $R_2$ are, independently, hydrogen, a halogen atom, hydroxy group, thiol group, an alkoxy group, a branched or linear alkyl group (e.g., a $C_1$–$C_{20}$ alkyl group), a branched or linear unsaturated hydrocarbon group, an ether group, nitro group, an amino group, a cycloalkyl group (e.g. a cyclohexyl group), or an aryl group (e.g., a phenyl or naphthyl group);

X is a linking group having the formula —$(CH_2)_m$—, branched or linear, where m is an integer between 0 and 50, inclusive, and one or more of the methylene groups is optionally replaced by a bond, an oxygen atom, a sulfur atom, a carbonyl group, an urethane group, an urea group, an ester group, an aryl group, a heterocyclic group, a $NR_4$ group, a $CHR_5$ group, or a $CR_6R_7$ group where $R_4$, $R_5$, $R_6$, and $R_7$ are, independently, H, an alkyl group, or an aryl group; and Y and Z are, independently, a carbazole group, a julolidine group, a (N,N-disubstituted)arylamine group such as a dialkarylamine group (e.g. dimethylphenylamine; methylethylphenylamine, dipropylphenylamine, ethylepropylphenylamine, ethylbutylnaphthylamine, etc.), an alkyldiarylamine group (e.g. methyldiphenylamino, ethyldiphenylamino, etc), and a triarylamino group (e.g., triphenyl amino, trinaphthylamino, etc), or any of their derivatives.

The charge transport compound may have more than two arms such that the linking group X may be linked to more than two hydrazone groups. The charge transport compound may or may not be symmetrical. Thus, for example, a portion of the linking group X attached to any given "arm" of the compound may be the same or different from the remaining portion of the linking groups attached to other "arms" of the compound. Similarly, the $R_1$ and $R_2$ groups may be the same or different and the Y and Z groups may be the same or different. In addition, the above-described formula for the charge transport compound is intended to cover isomers.

Another subgeneric Formula (XI) for this class of charge transport compound with only triarylamine R substituents has the formula

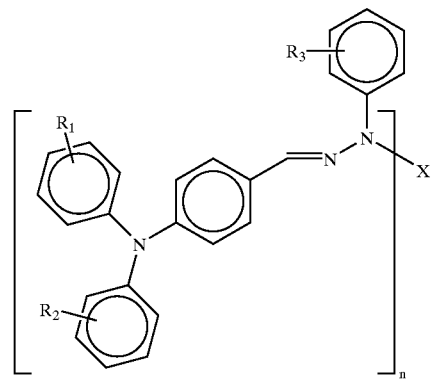

(XI)

where n is an integer between 2 and 6, inclusive;

$R_1$, $R_2$, and $R_3$ are, independently, hydrogen, a halogen atom, hydroxy group, thiol group, an alkoxy group, a branched or linear alkyl group (e.g., a $C_1$–$C_{20}$ alkyl group), a branched or linear unsaturated hydrocarbon group, an ether group, nitro group, an amino group, a cycloalkyl group (e.g. a cyclohexyl group), or an aryl group (e.g., a phenyl or naphthyl group); and X is a linking group having the formula —$(CH_2)_m$—, branched or linear, where m is an integer between 0 and 50, inclusive, and one or more of the methylene groups is optionally replaced by a bond, an oxygen atom, a sulfur atom, a carbonyl group, an urethane group, an urea group, an ester group, an aryl group, a heterocyclic group, a $NR_4$ group, a $CHR_5$ group, or a $CR_6R_7$ group where $R_4$, $R_5$, $R_6$, and $R_7$ are, independently, H, an alkyl group, or an aryl group. Specific and subgeneric central nucleus examples of Formula (XI) are represented by:

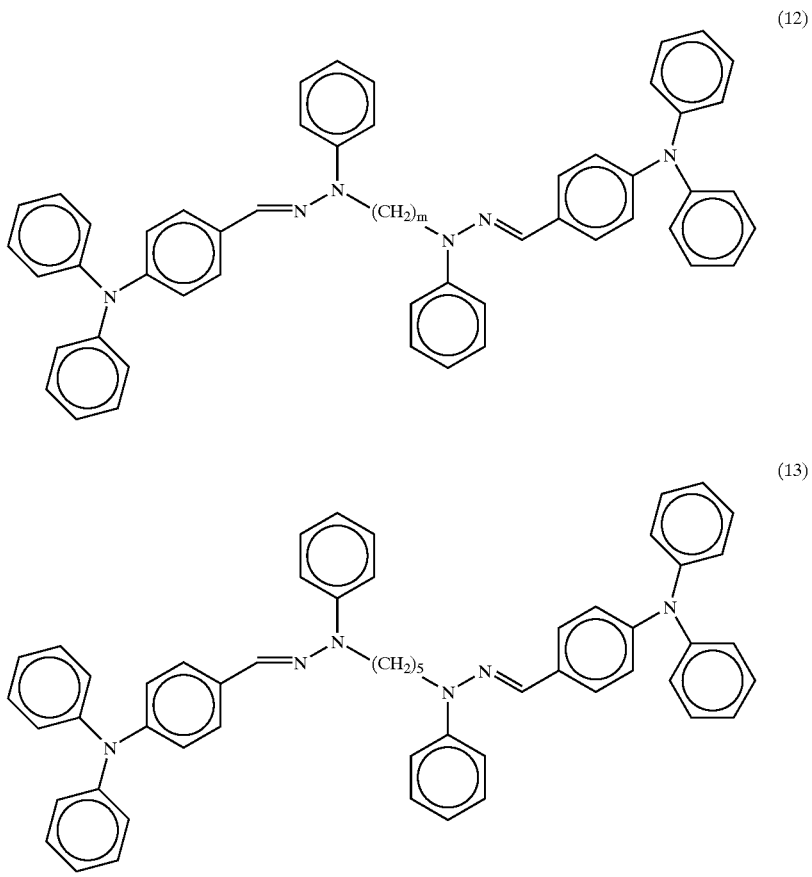

(12)

(13)

In a fifth aspect of the invention is the formation of charge transport compounds with at least three hydrazone moieties or groups attached to the bridging group. These compounds are represented by the general formula, falling within generic Formula I, of a charge transport compound having the formula:

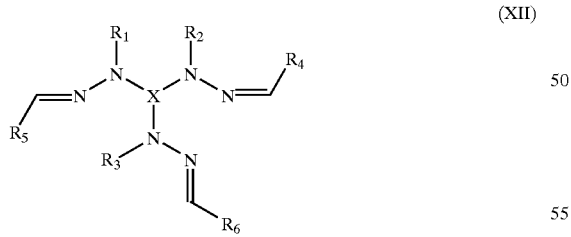

(XII)

$R_1$, $R_2$, and $R_3$ are, independently, a branched or linear alkyl group (e.g., a $C_1$–$C_{20}$ alkyl group), a branched or linear unsaturated hydrocarbon group, a cycloalkyl group (e.g. a cyclohexyl group), a heterocyclic group, or an aryl group (e.g., a phenyl or naphthyl group);

$R_4$, $R_5$, and $R_6$ are, independently, triarylamine (e.g., triphenylamine), diaryl alkylamine, dialkylarylamine (e.g., as described above as dialkarylamine), a carbocyclic ring such as anthraquinone, diphenoquinone, indane, or fluorenone, or a heterocyclic ring such as thiazoline, thiazolidine, phenothiazine, oxazoline, imidazoline, imidazolidine, thiazole, oxazole, isoxazole, oxazolidinone, morpholine, imidazole, benzothiazole, benzotriazole, benzoxazole, benzimidazole, naphthothiazole, naphthoxazole, naphthimidazole, quinoline (e.g., 2-quinoline or 4-quinoline), isoquinoline, quinoxaline, indole, indazole, pyrrole, purine, pyrrolidine, pyridine, piperidine, pyridazine, pyrazoline, pyrimidine, pyrazine, triazole, oxadiazole, tetrazole, urazole, carbazole, julolidine, or thiadiazole ring. These heterocyclic rings may also have substituents such as halogen atoms (e.g., chlorine, bromine and fluorine), alkyls (e.g., methyl, ethyl, n-propyl, isopropyl, n-butyl, sec-butyl, t-butyl, t-octyl, octyl, octadecyl, etc.), alkoxys (e.g., methoxy, ethoxy, butoxy, etc.), aryls (e.g., phenyl, tolyl, xylyl, etc.), aryloxys (e.g., phenoxy, methylphenoxy, chlorophenoxy, dimethylphenoxy, etc.), N-substituted aminos (e.g., N-methylamino, N-ethylamino, N-t-butylamino, N-octylamino, N-benzylamino, acetylamino, benzoylamino, etc.), N,N-disubstituted aminos (e.g., N,N-dimethylamino, N,N-diethylamino, N,N-dipropylamino, N,N-di-t-butylamino, N,N-dibenzylamino, N-ethyl-N-benzylamino, etc.), acyls (e.g., acetyl, propionyl, benzoyl, methylbenzoyl, dimethylbenzoyl, chlorobenzoyl, etc.), carbamoyl, sulfamoyl, nitro, cyano, hydroxy, carboxy, sulfonate, oxo, benzo, naptho, indeno, and phosphate; and X is a linking group having the formula

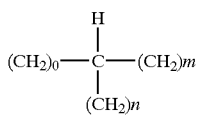

where m, n, and o is an integer between 0 and 50, inclusive; one or more of the methylene groups is optionally replaced by a bond, an oxygen atom, a sulfur atom, a carbonyl group, an urethane group, an urea group, an ester group, an aryl group, a heterocyclic group, a $NR_5$ group, a $CHR_6$ group, or a $CR_7R_8$ group where $R_5$, $R_6$, $R_7$, and $R_8$ are, independently, H, an alkyl group, or an aryl group; and the C—H group is optionally replaced by a nitrogen atom, a boron atom, a metal atom, and a $CR_9$ group where $R_9$ is an alkyl group or an aryl group.

A photoconductor system exits with a combination of (a) a charge transport compound and (b) a charge generating compound; and (c) an electrically conductive substrate.

The charge transport compound may have more than three arms such that the linking group X may be linked to more than three hydrazone groups. The charge transport compound may or may not be symmetrical. Thus, for example, a portion of the linking group X attached to any given "arm" of the compound may be the same or different from the remaining portion of the linking groups attached to other "arms" of the compound. Similarly, the $R_1$, $R_2$, and $R_3$ groups may be the same or different and the $R_4$, $R_5$, and $R_6$ groups may be the same or different. In addition, the above-described formula for the charge transport compound is intended to cover isomers.

The organophotoreceptor may be provided in the form of a plate, a disc, a flexible belt, a rigid drum, or a sheet around a rigid or compliant drum. In one embodiment, the organophotoreceptor includes: (a) a charge transport layer comprising the charge transport compound and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate.

In describing chemicals by structural formulae and group definitions, certain terms are used in a nomenclature format that is chemically acceptable. The terms groups, central nucleus, and moiety have defined meanings. The term group indicates that the generically recited chemical material (e.g., alkyl group, phenyl group, carbazole group, etc.) may have any substituent thereon which is consistent with the bond structure of that group. For example, alkyl group includes alkyl materials such as methyl ethyl, propyl iso-octyl, dodecyl and the like, and also includes such substituted alkyls such as chloromethyl, dibromoethyl, 1,3-dicyanopropyl, 1,3,5-trihydroxyhexyl, 1,3,5-trifluorocyclohexyl, 1-methoxydodecyl, and the like. However, as is consistent with such nomenclature, no substitution would be included within the term that would alter the fundamental bond structure of the underlying group. For example, where a phenyl ring group or central nucleus of a phenyl group is recited, substitution such as 1-hydroxyphenyl, 2,4-fluorophenyl, orthocyanophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Similarly, where the term a "central nucleus of the formula" is used and a structural formula is shown, any substituent may be provided on that formula, as long as the substitution does not alter the underlying bond structure of the formula (e.g., by requiring a double bond to be converted to a single bond, or opening a ring group, or dropping a described substituent group in the formula). Where the term "moiety" is used, such as alkyl moiety or phenyl moiety, that term indicates that the chemical material is not substituted.

In a sixth aspect, the invention features an electrophotographic imaging apparatus that includes (a) a plurality of support rollers; and (b) the above-described organophotoreceptor in the form of a flexible belt threaded around the support rollers. The apparatus preferably further includes a liquid toner dispenser.

In a seventh aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) contacting the surface with a liquid toner that includes a dispersion of colorant particles in an organic liquid to create a toned image; and (d) transferring the toned image to a substrate.

In an eighth aspect, the invention features a novel charge transport material having the formula (XIII)

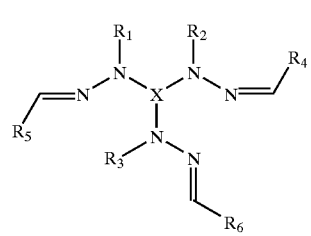

$R_1$, $R_2$, and $R_3$ are, independently, described above;
$R_4$, $R_5$, and $R_6$ are, independently, as described above;
X is a linking group having the formula

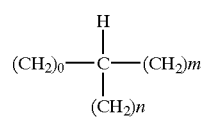

where m, n, and o are as described above.

Specific examples of suitable charge transport compounds have the following formulae:

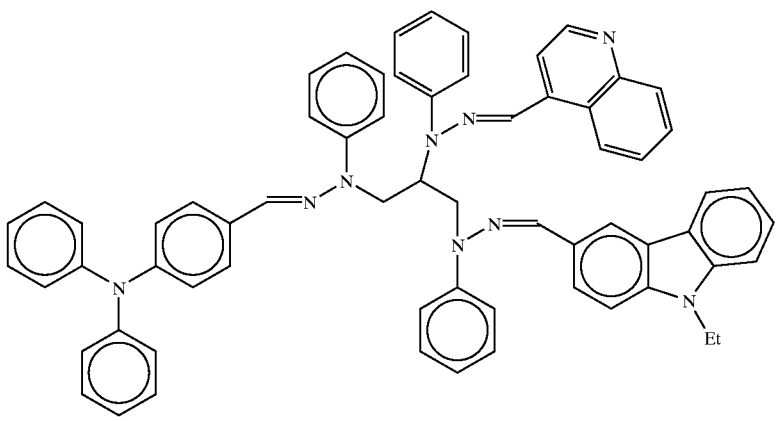

(14)

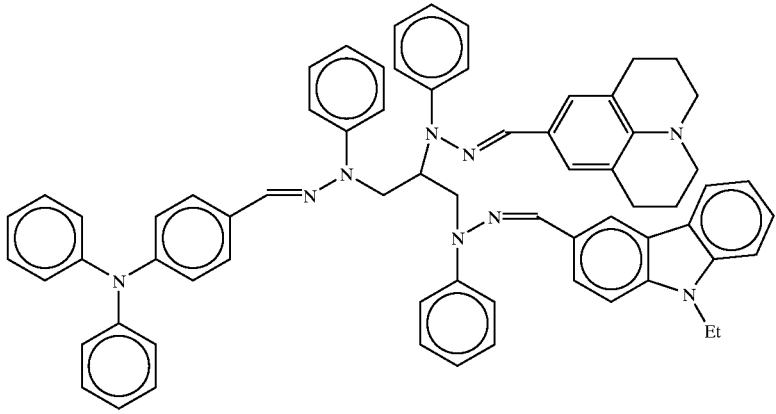

(15)

The charge transport compounds according to Formulae (I)–(XIII) may be prepared by a multi-step synthesis using a combination of known synthetic techniques.

The first step is the preparation of one or more of aldehyde derivative of any heterocyclic compound, preferably carbazole, triphenylamine, or julolidine (heterocyclic group, preferably a heterocyclic group selected from the group consisting of julolidine ring groups, carbazole ring groups, diarylamine groups (e.g., forming N,N-diaryl-substituted) amine groups, dialkarylamine groups (e.g., also referred to as dialkylarylamine groups such as dimethylphenylamine; methylethylphenylamine, dipropylphenylamine, ethylepropylphenylamine, ethylbutylnaphthylamine, etc.), triarylamino groups (e.g., triphenyl amino, trinaphthylamino), and triarylmethane ring groups (examples of other heterocyclic groups being the following non-limiting list of such as thiazoline, thiazolidine, phenothiazine, oxazoline, imidazoline, imidazolidine, thiazole, oxazole, isoxazole, oxazolidinone, morpholine, imidazole, benzothiazole, benzotriazole, benzoxazole, benzimidazole, naphthothiazole, naphthoxazole, naphthimidazole, quinoline (e.g., 2-quinoline or 4-quinoline), isoquinoline, quinoxaline, indole, indazole, pyrrole, purine, pyrrolidine, pyridine, piperidine, pyridazine, pyrazoline, pyrimidine, pyrazine, triazole, oxadiazole, tetrazole, urazole, carbazole, julolidine, or thiadiazole ring) by Vilsmeier reaction between carbazole, triphenylamine, or julolidine correspondingly and phosphorus oxychloride (POCl$_3$). Carbazole, triphenylamine, diarylamine, triarylamine, trinaphthylmine, or julolidine is dissolved in N,N-dimethylformamide (DMF) and then the solution is cooled. Then POCl$_3$ (10–15% excess) is added slowly via a dropping funnel to the cooled DMF solution.

The second step is the reaction between phenylhydrazine and one of the aldehyde derivative of carbazole, triphenylamine, diarylamine, triarylamine, trinaphthylamine, or julolidine in a molar ratio of 1:1 to form the corresponding hydrazone derivative by refluxing the reactants in tetrahydrofuran (THF) for two hours. More than one hydrazone derivative may be prepared if an unsymmetrical charge transport compound is desired.

The last step is the reaction of one of the hydrazone with a dibromoalkane in a molar ratio of 2:1 to form a symmetrical charge transport compound. The hydrazone obtained is dissolved in dimethyl sulfoxide (DMSO). After the addition of 25% aqueous solution of NaOH, a dibromoalkane is added to the solution. This solution is stirred at 70° C. for approximately 1 hour. The product from this reaction is purified by recrystallization. If an unsymmetrical charge transport compound is desired, two or more different hydrazones are used. Each hydrazone will react, one at a time, with a dibromoalkane or an alkane with more than two bromo groups in a molar ratio of 1:1 under condition described above.

Formula 12 may be prepared by the condensation reaction of 4-(diphenylamino)-benzaldehyde with phenyl hydrazine; and then by a nucleophilic substitution reaction of the product of the condensation reaction with a dibromoalkane to form the final dimeric charge transport material. Specifically, Compound 13 may be prepared according to the above synthesis wherein the dibromoalkane is 1,5-dibromopentane.

The invention provides novel charge transport materials for organic photoreceptors featuring a combination of good mechanical and electrostatic properties. These photoreceptors can be used successfully with liquid or dry toners to produce high quality images. The high quality of the images is maintained after repeated cycling.

Other features and advantages of the invention will be apparent from the following description of the preferred embodiments thereof, and from the claims.

The invention features organic photoreceptors that include charge transport compounds having the formulae set forth in the Summary of the Invention above. The charge transport compounds according to Formula (I) may be prepared by a multi-step synthesis using a combination of known synthetic techniques. For example, the general synthetic method for synthesis of Compounds 4–6 was according to a 4-step synthetic procedure. The first step is N-alkylatation of carbazole to introduce an alkyl group to the carbazole nitrogen. The second step is the formation of a —CHO group on the carbazole ring by Vilsmeier reaction. The third step is the formation of hydrazone by the reaction of the product from step 2 with a hydrazine. The last step is a nucleophilic substitution reaction to form a bridging group between two or more hydrazone moieties. Compounds 1–3 were prepared according to the above procedure except the first and second steps were skipped because the starting materials for step three are commercially available.

The organophotoreceptor may be in the form of a plate, drum, or belt, with flexible belts being preferred. The organophotoreceptor may include an electrically conductive substrate and a photoconductive element in the form of a single layer that includes both the charge transport compound and charge generating compound in a polymeric binder. Preferably, however, the organophotoreceptor includes an electrically conductive substrate and a photoconductive element that is a bilayer construction featuring a charge generating layer and a separate charge transport layer. The charge generating layer may be located intermediate the electrically conductive substrate and the charge transport layer. Alternatively, the photoconductive element may be an inverted construction in which the charge transport layer is intermediate the electrically conductive substrate and the charge generating layer.

The electrically conductive substrate may be flexible, for example in the form of a flexible web, sheet, or a belt, or inflexible, for example in the form of a drum or a sheet wrapped around a drum. Typically, a flexible electrically conductive substrate comprises of an insulated substrate and a thin layer of electrically conductive materials. The insulated substrate may be paper or a film forming polymer such as polyethylene terephthalate, polyimide, polysulfone, polyethylene naphthalate, polypropylene, nylon, polyester, polycarbonate, polyvinyl fluoride, polystyrene and the like. Specific examples of supporting substrates included polyethersulfone (Stabar® S-100, available from ICI), polyvinyl fluoride (Tedlar®, available from E. I. DuPont de Nemours & Company), polybisphenol-A polycarbonate (Makrofol®, available from Mobay Chemical Company) and amorphous polyethylene terephthalate (Melinar®, available from ICI Americas, Inc.). The electrically conductive materials may be graphite, dispersed carbon black, iodide, conductive polymers such as polypyroles and Calgon® Conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. Preferably, the electrically conductive material is aluminum. Typically, the photoconductor substrate will have a thickness adequate to provide the required mechanical stability. For example, flexible web substrates generally have a thickness from about 0.01 to about 1 mm, while drum substrates generally have a thickness of from about 0.5 mm to about 2 mm. Typical structures for polycarbonates include:

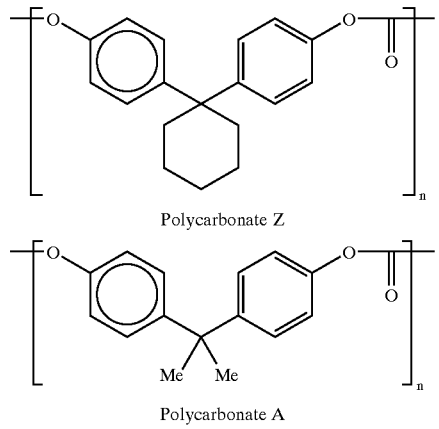

Polycarbonate Z

Polycarbonate A

The charge generating compound is a material which is capable of absorbing light to generate charge carriers, such as a dyestuff or pigment. Examples of suitable charge generating compounds include metal-free phthalocyanines, metal phthalocyanines such as titanium phthalocyanine, copper phthalocyanine, oxytitanium phthalocyanine, hydroxygallium phthalocyanine, squarylium dyes and pigments, hydroxy-substituted squarylium pigments, perylimides, polynuclear quinones available from Allied Chemical Corporation under the tradename Indofast Double Scarlet, Indofast Violet Lake B, Indofast Brilliant Scarlet and Indofast Orange, quinacridones available from DuPont under the tradename Monastral Red, Monastral Violet and Monastral Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9, 10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulfoselenide, cadmiumselenide, cadmium sulfide, and mixtures thereof. Preferably, the charge generating compound is oxytitanium phthalocyanine, hydroxygallium phthalocyanine or a combination thereof.

Preferably, the charge generation layer comprises a binder in an amount of from about 10 to about 90 weight percent and more preferably in an amount of from about 20 to about 75 weight percent, based on the weight of the charge generation layer.

The binder is capable of dispersing or dissolving the charge transport compound (in the case of the charge transport layer) and the charge generating compound (in the case of the charge generating layer). Examples of suitable binders for both the charge generating layer and charge transport layer include polystyrene-co-butadiene, modified acrylic polymers, polyvinyl acetate, styrene-alkyd resins, soyaalkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly (hydroxyether) resins, polyhydroxystyrene resins, novolak, poly(phenylglycidyl ether)-co-dicyclopentadiene, copolymers of monomers used in the above-mentioned polymers, and combinations thereof. Polycarbonate binders are particularly preferred. Examples of suitable polycarbonate binders include polycarbonate A which is derived from bisphenol-A, polycarbonate Z, which is derived from cyclohexylidene bisphenol, polycarbonate C, which is derived from methylbisphenol A, and polyestercarbonates.

The photoreceptor may include additional layers as well. Such layers are well-known and include, for example, barrier layers, release layers, adhesive layer, and sub-layer. The release layer forms the uppermost layer of the photoconductor element with the barrier layer sandwiched between the release layer and the photoconductive element. The adhesive layer locates and improves the adhesion between any of the additional layers. The sub-layer is a charge blocking layer and locates between the electrically conductive substrate and the photoconductive element. The sub-layer may also improve the adhesion between the electrically conductive substrate and the photoconductive element.

Suitable barrier layers include coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyninyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above organic binders optionally may contain small inorganic particles such as fumed silica, silica, titania, alumina, zirconia, or a combination thereof. The typical particle size is in the range of 0.001 to 0.5 micrometers, preferably 0.005 micrometers. A preferred barrier layer is a 1:1 mixture of methyl cellulose and methyl vinyl ether/maleic anhydride copolymer with glyoxal as a crosslinker.

The release layer topcoat may comprise any release layer composition known in the art. Preferably, the release layer is a fluorinated polymer, siloxane polymer, fluorosilicone polymer, silane, polyethylene, polypropylene, or a combination thereof. More preferably, the release layers is crosslinked silicone polymers.

Typical adhesive layers include film forming polymers such as polyester, polyvinylbutyral, polyvinylpyrolidone, polyurethane, polymethyl methacrylate, poly(hydroxy amino ether) and the like. Preferably, the adhesive layer is poly(hydroxy amino ether). If such layers are utilized, they preferably have a dry thickness between about 0.01 micrometer and about 5 micrometers.

Typical sub-layers include polyvinylbutyral, organosilanes, hydrolyzable silanes, epoxy resins, polyesters, polyamides, polyurethanes, silicones and the like. Preferably, the sub-layer has a dry thickness between about 20 Angstroms and about 2,000 Angstroms.

The charge transport compounds, and photoreceptors including these compounds, are suitable for use in an imaging process with either dry or liquid toner development. Liquid toner development is generally preferred because it offers the advantages of providing higher resolution images and requiring lower energy for image fixing compared to dry toners. Examples of useful liquid toners are well-known. They typically include a colorant, a resin binder, a charge director, and a carrier liquid. A preferred resin to pigment ratio is 2:1 to 10:1, more preferably 4:1 to 8:1. Typically, the colorant, resin, and the charge director form the toner particles.

The invention will now be described further by way of the following examples.

EXAMPLES

A. Synthesis

Charge transport compounds were synthesized as follows. The number associated with each compound refers to the number of the chemical formula set forth in the Summary of the Invention above.

Compound (1)

To a 2-liter 3-neck round bottom flask equipped with mechanical stirrer and reflux condenser and heating mantle were added 9-ethyl-3-carbazolecarboxyaldehyde (1 mole, 223.28 g, obtained commercially from Aldrich Chemical Company) and tetrahydrofuran (600 ml). Heating was applied to ensure that all solid entered into solution. Phenyl hydrazine (119 g, 1.1 mole, obtained commercially from Aldrich Chemical Company) was added and the mixture was refluxed for 2 hours. When thin layer chromatography (TLC) showed the total disappearance of the starting material and the formation of the product, the flask was allowed to cool to room temperature and the solvent was evaporated. The solid was filtered of, washed with 20 ml of ethanol and dried. A yellow solid was obtained (263 g, 80% yield).

To a 250 ml 3-neck round bottom flask equipped with thermometer and mechanical stirrer were added the yellow solid (0.1 mole, 33.14 g) prepared above and DMSO (50 ml). After the solid was dissolved, 1,10-dibromodecane (15 g, 0.05 mole, obtained commercially from Aldrich Chemical Company) was added. An aqueous solution of 50% NaOH (20 g) was added and heated to 85° C. for 2 hours. The mixture was cooled to room temperature and then added to 2 L of water. A light yellow solid was precipitated out, filtered, washed with water, and dried. The yield was 49 g (61%); m.p. 119° C. The $^1$H-NMR spectrum of the solid shows peaks at 1.26–1.52 ppm (m; 16H); 1.62–1.84 ppm (m; 4H); 3.82–4.01 ppm (t; 4H); 4.25–4.47 ppm (q, 6H); 6.85–6.96 ppm (t; 2H); 7.09–7.25 ppm (m; 2H); 7.29–7.54 ppm (m; 12H); 7.70–7.79 ppm (s; 2H); 7.86–7.98 ppm (dd; 2H); 8.08–8.19 ppm (d; 2H); 8.28–8.38 ppm (d; 2H). The $^1$H-NMR spectrum is in full agreement with the structure of Compound (1).

Compound (2)

Compound (2) was prepared according to the procedure of Compound (1) except that 1,10-dibromodecane (0.05 mole) was replaced with 1,5-dibromodecane (0.05 mole, obtained commercially from Aldrich Chemical Company). The yield was 65%; m.p. 203° C. The $^1$H-NMR spectrum of the solid shows peaks at 1.35–1.49 ppm (t; 6H); 1.60–1.75 ppm (m; 2H); 1.77–1.97 ppm (m; 4H); 3.93–4.10 ppm (t; 4H); 4.28–4.44 ppm (q; 4H); 6.86–6.98 ppm (t; 2H); 7.28–7.53 ppm (m; 14H); 7.73–7.82 ppm (s; 2H); 7.88–7.99 ppm (dd; 2H); 8.06–8.17 ppm (d; 2H); 8.28–8.39 ppm (d, 2H). The $^1$H-NMR spectrum is in full agreement with the structure of Compound (2).

Compound (3)

Compound (3) was prepared according to the procedure of Compound (1) except that 1,10-dibromodecane (0.05 mole) was replaced with 1,4-dibromodecane (0.05 mole, obtained commercially from Aldrich Chemical Company). The yield was 70%; m.p.207° C. The $^1$H-NMR spectrum of the solid shows peaks at 1.33–1.50 ppm (t; 6H); 1.80–2.06 ppm (m; 4H); 3.92–4.16 ppm (m; 4H ); 4.21–4.51 ppm (q=4H); 6.87–7.03 ppm (t=2H); 7.10–7.24 ppm (m; 2H); 7.27–7.60 ppm (m; 14H); 7.72–7.82 ppm (s; 2H); 7.87–7.98 ppm (dd; 2H); 8.04–8.19 ppm (d; 2H); 8.27–8.39 ppm (s; 2H). The $^1$H-NMR spectrum is in full agreement with the structure of Compound (3).

Compound (4)

To a 3-liter 3-neck round bottom flask equipped with a reflux condenser and a mechanical stirrer were added carbazole (177.78 g, 1.063 mole, obtained commercially from Aldrich Chemical Company), 1-bromoheptane (200 g, 1.117 mole, obtained commercially from Aldrich Chemical Company), benzyltriethylammonium chloride (12.00 g, 0.053 mole, obtained from Aldrich Chemical company) and toluene (800 ml). The mixture was stirred at room temperature for 30 minutes. Then the mixture was refluxed for 5 hours after 50% NaOH aqueous solution (400 g) was added. The mixture was cooled to room temperature and an organic phase appeared. The organic phase was separated, washed with water, dried over Magnesium sulfate ($Mg_2SO_4$), filtered, and evaporated to remove all solvent. An oil was obtained. The yield was 78% (220 g). A $^1$H-NMR spectrum was recorded and it was in agreement with the structure of N-heptylcarbazole.

To a 1-liter 3-neck round bottom flask equipped with a mechanical stirrer, a dropping funnel, and a thermometer were added N-heptylcarbazole (282 g, 1.062 mole, prepared in the previous step) and DMF (500 ml). The flask was placed on ice bath until temperature inside is 5° C., then $POCl_3$ (109 g, 1.17 mole) was added dropwise via the dropping funnel. During the addition the temperature was not allowed to rise above 5° C. After the addition was completed, the flask was placed in a boiling water bath for 2 hours. Then the solution in the flask was cooled to room temperature and added to a large volume of water (3 liter). The solid was filtered off, washed repeatedly with water, and dried. The yield was 75%. A $^1$H-NMR spectrum was recorded and it was in agreement with 9-heptylcarbazole-3-carboxyaldehyde.

To a 2-liter 3-neck round bottom flask equipped with mechanical stirrer and reflux condenser and heating mantle were added 9-heptylcarbazole-3-carboxyaldehyde (1 mole, 293.45 g) and 600 ml of tetrahydrofuran. Heating was applied to ensure that all solid entered into solution. Phenyl hydrazine (119 g, 1.1 mole, obtained commercially from Aldrich Chemical Company) was added and the mixture was refluxed for 2 hours. When TLC showed the total disappearance of the starting material and the formation of the product, the flask was allowed to cool to room temperature and the solvent was evaporated. The solid was filtered of, washed with 20 ml of ethanol and dried. A yellow solid was obtained (249 g, 83% yield).

To a 250 ml 3-neck round bottom flask equipped with thermometer and mechanical stirrer were added the yellow solid (0.1 mole, 38.36 g) prepared above and 50 ml of DMSO. After the solid was dissolved, 1,10-dibromodecane (15 g, 0.05 mole) was added. An aqueous solution of 50% NaOH (20 g) was added and heated to 85° C. for 2 hours. The mixture was cooled to room temperature and then added to 2 L of water. A light yellow solid was precipitated out, filtered, washed with water, and dried. The yield was 25 g (55%); m.p. 116° C. The $^1$H-NMR spectrum of the solid shows peaks at 0.70–0.96 ppm (t; 6H); 1.01–1.62 ppm (m; 28H); 1.64–2.00 ppm (m; 8H); 3.80–4.06 ppm (t; 4H); 4.18–4.42 ppm (t; 4H); 6.77–7.00 ppm (t; 2H); 7.12–7.29 ppm (m; 4H); 7.28–7.58 ppm (m; 12H); 7.67–7.81 ppm (s; 2H); 7.85–8.01 ppm (dd; 2H); 8.07–8.22 ppm (d; 2H); 8.26–8.43 ppm (s; 2H). The $^1$H-NMR spectrum is in full agreement with the structure of Compound (4).

Compound (5)

Compound (5) was prepared according to the procedure of Compound (4) except that 1,10-dibromodecane was replaced with 1,5-dibromodecane. The yield was 45%, m.p. 120° C. The $^1$H-NMR spectrum of the solid shows peaks at 0.69–0.95 ppm (t; 6H); 1.05–1.49 ppm (m; 20H); 1.75–1.98 ppm (m; 6H); 3.84–4.12 ppm (t; 4H); 4.16–4.40 ppm (t; 4H); 6.86–7.00 ppm (t; 2H); 7.15–7.29 ppm (m; 4H); 7.37–7.51 ppm (m; 12H); 7.71–7.83 ppm (s; 2H); 7.88–8.00 ppm (dd; 2H); 8.06–8.19 ppm (d; 2H); 8.26–8.40 ppm (s, 2H). The $^1$H-NMR spectrum is in full agreement with the structure of Compound (5).

Compound (6)

Compound (6) was prepared according to the procedure of Compound (5) except that 1-bromoheptane was replaced with 1-bromo-3-propylbenzene. The yield was 60%, m.p. 184° C. The $^1$H-NMR spectrum is in full agreement with the structure of Compound (6).

B. $^1$H NMR Measurements

The $^1$H-NMR spectra were obtained by a 300 MHz Bruker NMR spectrometer (obtained commercially from Bruker Instruments Inc., Billerica, Mass.) using $CDCl_3$ solvent with 0.03% v/v tetramethylsialine (obtained commercially from Aldrich Chemical Company) as the internal reference. The following abbreviations were used: s=singlet; d=doublet; dd=double doublet; m=multiplet; q=quartet; and t=triplet.

C. Thermal Transitions

Thermal transition data for various charge transport materials was collected using a TA Instruments Model 2929 Differential Scanning Calorimeter (New Castle, Del.) equipped with a DSC refrigerated cooling system (–70° C. minimum temperature limit), and dry helium and nitrogen exchange gases. The calorimeter ran on a Thermal Analyst 2100 workstation with version 8.10B software. An empty aluminum pall was used as the reference.

Samples were tested both neat and as a mixture with Polycarbonate Z ("PCZ"). The neat samples were prepared by placing 4.0 to 8.0 mg of neat charge transport material into an aluminum sample pan and crimping the upper lid to produce a hermetically sealed sample for DSC testing. The results were normalized on a per mass basis.

The Polycarbonate Z-mixed samples were prepared by filling the bottom portion of the aluminum sample pan to capacity with a 15–20% solids solution of the charge transport material in Polycarbonate Z, followed by air-drying overnight. Each air-dried sample was then placed in a convection oven at 50–55° C. for another 24–48 hours to eliminate trace solvent, after which the upper sample lid was crimped on to produce a hermetically sealed sample for DSC testing. Typical sample size was 7.0 to 15.0 mg. Again, the results were normalized on a per mass basis.

Each sample was subjected to the following protocol to evaluate its thermal transition behavior:
1. Equilibrate at 0° C. (Default—Nitrogen Heat Exchange Gas);
2. Isothermal for 5 min.;
3. External Event: Nitrogen Heat Exchange Gas;
4. Ramp 10.0° C./min. to a temperature 30° C. above the melting point of the charge transport material;
5. External Event: Helium Heat Exchange Gas;

6. Isothermal for 5 min.;
7. Ramp 10.0° C./min. to 0° C.;
8. External Event: Nitrogen Heat Exchange Gas;
9. Isothermal for 5 min.;
10. Ramp 10.0° C./min. to a temperature 40° C. above the melting point of the charge transport material;
11. External Event: Helium Heat Exchange Gas;
12. Isothermal for 5 min.;
13. Ramp 10.0° C./min. to 0° C.;
14. External Event: Nitrogen Heat Exchange Gas;
15. Isothermal for 5 min.;
16. Ramp 10.0° C./min. to 275° C.

The first cycle (steps 1–7) was used to (a) remove the thermal history of the sample, (b) obtain the melting transition for crystalline charge transport materials, and (c) obtain a homogeneous charge transport material/ Polycarbonate Z mixture in the event the charge transport material crystallized during sample preparation. A homogeneous mixture is obtained only if the charge transport material (melt or cast) is miscible with the Polycarbonate-Z.

The second cycle (steps 8–13) was used to identify the glass transition temperature and charge transport material recrystallization or melting transitions.

The third cycle (steps 14–16) was used to report the final thermal transitions.

The results are shown below in Table 1. All temperatures are reported in ° C. "CTM" refers to the charge transport compound. "PCZ" refers to Polycarbonate Z binder.

TABLE 1

| Compound | M.p (° C.) | Tg without binder (° C.) | Tg with 50% PCZ (° C.) |
|---|---|---|---|
| 1 | 119 | 46 | 83.7 |
| 2 | 203 | 84.4 | 102.5 |
| 3 | 207 | 79.1 | NA |
| 4 | 116 | 29.3 | 56.9 |
| 5 | 120 | 44.5 | 78.3 |
| 6 | 184 | 57.4 | NA |

As expected, an increase in the aliphatic chain length of $R_1$ (in Formula I) from ethyl to heptyl lowers the Tg (compare Compound (2) with Compound (5)). Also, an increase in the chain length of the X-Y linkage (in Formula I) from pentyl to decyl also lowers the Tg (Compare Compounds (2) with (1)). In the presence of polycarbonate Z binder, the Tg of Compounds (3) and (6) could not be measured due to phase separation of the CTM from the binder.

D. Organic Photoreceptor Preparation Methods (i) Die Coating

A charge transport solution containing 50 wt. % of a selected charge transport compound in Polycarbonate Z binder (obtained commercially from Mitsubishi Gas Chemical under the designation "Lupilon Z-200" resin) was prepared by combining a solution of either 10.0 g or 15.0 g, depending upon solubility, of the charge transport compound in 120.0 g of tetrahydrofuran with 15.0 g of Polycarbonate Z and 0.03 g of Dow Corning 510 Fluid. The charge transport solution was then die coated onto 3 mil (76 micrometer) thick polyethylene terephthalate (PET) film (Melinex 442 polyester film from Dupont) having a 1 ohm/square aluminum vapor coat and an additional 0.25 micrometer thick PET sub-layer overlaying the aluminum vapor coat. The purpose of including the PET sub-layer was to improve adhesion and prevent charge injection into the charge transport layer. The dried charge transport layer had a nominal thickness of 8.75 micrometers. Die coating (also known as slot coating) techniques are described by E. Cohen and E. Gutoff, *Modern Coating and Drying Technology*, VCH Publishers, Inc. New York, 1992, pp. 117–120.

A dispersion was prepared by micronising 32.6 g of oxytitanium phthalocyanine pigment (obtained commercially from H. W. Sands Corp., Jupiter, Fla.), 32.6 g of S-Lec B Bx-5 polyvinyl butyral resin (obtained commercially from Sekisui Chemical Co. Ltd.), and 684.4 g of 2/1 (w/w) methyl ethyl ketone/toluene using a horizontal sand mill operating in recirculation mode for 8 hours. This stock solution was diluted to 3.5 wt. % solids by adding 1113 g of 2:1 (w/w) methyl ethyl ketone/toluene prior to coating. The resulting dispersion was die coated onto the charge transport layer and dried to form a charge generating layer having a nominal thickness of 0.27 micrometer. This dual layer organic photoconductor was then overcoated with a barrier layer.

Two different barrier layer solutions were used. The first ("Barrier A") was prepared by mixing 86.3 g of 3% Methocel A15L V in water, 86.3 g of 3% Gantrez AN-169 polymer (obtained commercially from ISP Technologies) in water, 172.44 g of methanol, 0.65 g of 40% Glyoxal 40 in water, and 0.07 g Triton X-100 surfactant. The other barrier layer solution ("Barrier B") was prepared by combining 217.6 g of 6% S-Lec Bx-5 polyvinyl butyral resin, 1385.7 g isopropyl alcohol, 33.5 g Nalco 1057 colloidal silica, 33.1% Z-6040 silane (Dow Corning 50/50 (w/w) in isopropyl alcohol/water), and 130.17 g Gantrez AN-169 polymer following the procedure described in U.S. Pat. No. 5,733, 698.

The barrier layer solution was slot-die coated onto the dual layer organic photoconductor and dried to form a layer having a nominal thickness of 0.4 micrometer.

ii. Lamination

Inverted dual layer organophotoreceptors were prepared incorporating compounds 1–6 as charge transport material. A charge transport solution containing 50 wt. % of a selected charge transport compound in Polycarbonate Z binder was prepared by combining a solution of 1.25 g of the charge transport compound in 8.0 g of tetrahydrofuran with 1.25 g of Polyearbonate Z in 2.50 g of toluene. The charge transport solution was then hand-coated with a Meyer rod (#36) onto a 3 mil (76 micrometer) thick aluminized polyethylene terephthalate film (Melinex® 442 polyester film from Dupont having a 1 ohm/square aluminum vapor coat) having a 0.3 micron polyester resin sub-layer (Vitel® PE-2200 from Bostik, Middletown, Mass.) and dried to form a charge transport layer having a thickness of 9 micrometers.

A dispersion was prepared by micronising 1.35 g of oxytitanium phthalocyanine pigment (H. W. Sands Corp., Jupiter, Fla.), 1.35 g of S-Lec B Bx-5 polyvinylbutryal resin (Sekisui Chemical Co. Ltd.), 26 g of methyl ethyl ketone, and 13 g of toluene using a horizontal sand mill operating in recirculation mode for 8 hours. The resulting dispersion was then slot-die coated onto unsubbed 2 mil (51 micrometer) thick polyethylene terephthalate (PET) film and dried at 80° C. for 10 minutes to form a charge generating layer having a thickness of 0.27 micrometer on the PET film.

The charge transport layer and the charge generating layer were laminated together at 140° C. using a Model 447 Matchprint™ Laminator (obtained commercially from Imation Corp., Oakdale, Minn.). After lamination, the 2 mil (51 micrometer) PET film was peeled off the surface of the charge generation layer to form the inverted dual layer organophotoreceptor.

E. Solubility Testing

Solubility testing of each individual charge transport compound was performed at room temperature using tetrahydrofuran as the solvent. Solubility results were reported as the percent solids of saturated solution. In general, it is desirable to maximize the solubility value.

F. Electrostatic Testing

Electrostatic testing was performed on a number of inverted dual layer organic photoreceptor samples. The samples were prepared either by lamination or by die coating.

Electrostatic testing of compounds 1–6 was performed and recorded at ambient temperature on a QEA PDT-2000 instrument (commercially available from Quality Engineering Associates, Inc., Burlington, Mass.). Charge-up was performed at 8 kV. Discharge was performed by exposing the photoreceptor to a 780 nm-filtered tungsten light source down a fiber optic cable. Each sample was exposed to 2 microjoules/cm$^2$ of energy for 0.05 seconds; the total exposure intensity was 20 microwatts/cm$^2$. After charge-up, the acceptance voltage ($V_{acc}$) was measured in volts. This value was recorded as $V_{acc}$ after one cycle. Following this initial charge-up, a one second dark decay followed before the sample was discharged with the 0.05 second light pulse of 2 microjoules/cm$^2$ at 780 nm, after which the residual voltage ($V_{res}$) was measured in volts. This value was recorded as $V_{res}$ after one cycle. $V_{acc}$ and $V_{res}$ were also measured after a total of 1000 cycles. In general, it is desirable to maximize $V_{acc}$ and to minimize $V_{res}$.

TABLE 2

| Compound | $V_{acc}$ (V) | Dark Decay (V) | Discharge (V) | $V_{res}$ (V) |
|---|---|---|---|---|
| 5 | 575 | 64 | 398 | 58 |
| 6 | 512 | 109 | 393 | 50 |
| 1 | 596 | 38 | 89 | 468 |
| 4 | 560 | 151 | 322 | 91 |

The data in Table 2 indicate that these charge transport materials are suitable for making photoreceptors.

Examples 8–10

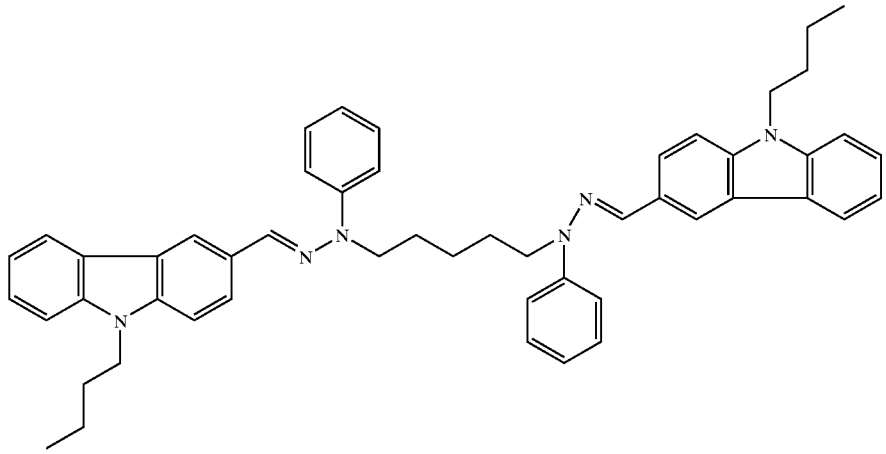

(8)

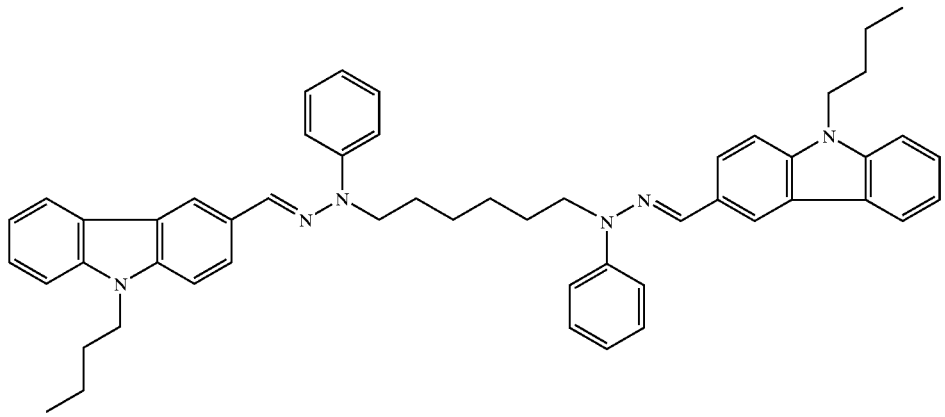

(9)

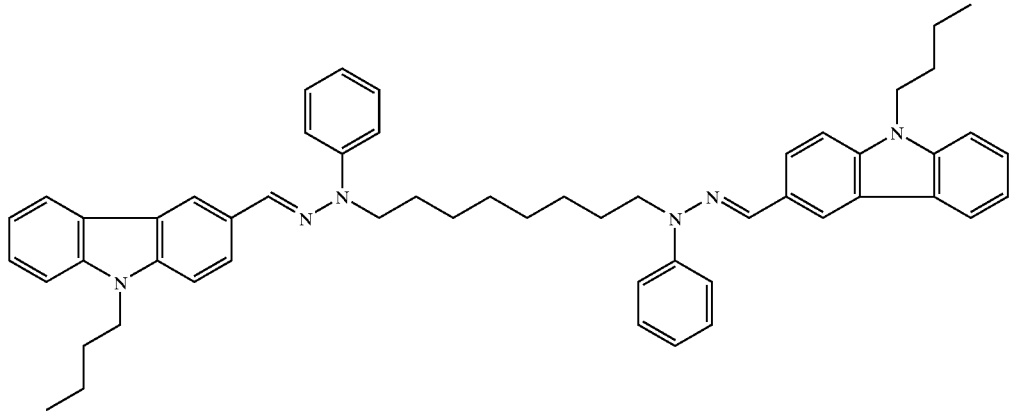

(10)

Compound (8)

To a 5-liter 3-neck round bottom flask equipped with a reflux condenser, mechanical stirrer and heating mantle were added carbazole (579.62 g, 3.47 mole, obtained from Aldrich Chemical Company, Milwaukee, Wis.), 1-bromo butane (500 g, 3.65 mole, obtained from Aldrich Chemical Company, Milwaukee, Wis.), benzyltriethylammonium chloride (39.48 g, 0.17 mole, obtained from Aldrich Chemical Company, Milwaukee, Wis.), and toluene (3 liter). The mixture was stirred at room temperature for 30 minutes. Then 50% NaOH aqueous solution (1300 g) was added and the mixture was refluxed for five hours. The mixture was cooled to room temperature and the organic phase was separated, washed with water and dried over magnesium sulfate, filtered, and evaporated to remove all solvent. A liquid product was obtained. The yield was 644 g (83%). The $^1$H-NMR spectrum of the product in this step in $CDCl_3$ was in agreement with the structure of N-butylcarbazole.

To a 3-liter, 3-neck round bottom flask equipped with a mechanical stirrer, dropping funnel, and a thermometer were added N-butylcarbazole (644 g, 2.88 mole, prepared in the previous step) and DMF (1300 ml). The flask was placed in ice bath until the temperature inside the flask is 5° C., then $POCl_3$ (498 g, 3.25 mole, obtained from Aldrich Chemical Company) was added dropwise via the dropping funnel. During the addition, the temperature was not allowed to rise above 5° C. The solution in the flask was cooled to room temperature and added to large volume of water (3 Liter). The solid was filtered of, washed repeatedly with water and dried. The yield was 668 g (92%). The $^1$H-NMR spectrum of the product in this step in $CDCl_3$ was in full agreement with the structure of 9-butylcarbazole-3-carboxaldyde.

To a 2-liter 3-neck round bottom flask equipped with mechanical stirrer and reflux condenser and heating mantle were added 9-butylcarbazole (668 g, 2.66 mole, obtained from the previous step) and 500 ml of toluene, phenyl hydrazine (316.4 g, 2.93 mole, obtained from Aldrich Chemical Company). The mixture was refluxed for 2 hours. Thin layer chromatography (TLC) showed the total disappearance of the starting material and the formation of the product. The flask was cooled to room temperature and the solid was collected, washed with 100 ml of ethanol and dried. The yield was 773 g (85%). The $^1$H-NMR spectrum of the product in this step in $CDCl_3$ was in agreement with the expected product.

To a 250 ml 3-neck round bottom flask equipped with thermometer and mechanical stirrer were added the product from the previous step (34.15 g, 0.1 mole) and 50 ml of DMSO. After the solid was dissolved, 1,5-dibromoheptane (11.5 g, 0.05 mole, obtained from Aldrich Chemicals Company) was added. An aqueous solution of 50% NaOH (20 g) was added and the mixture was heated to 85° C. for two hours. The mixture was cooled to room temperature and then added to 2 L of water. A gummy solid was formed which solidified upon standing at room temperature, which was washed repeatedly with water and dried. A crude product (20 g) was obtained. The product was recrystallized 4 times from ethyl acetate with activated charcoal and silica. A light yellow solid was obtained which was dried in vacuum oven (80° C.) for six hours. The melting point was found to be 182–183° C. The $^1$H-NMR of the final product in $CDCl_3$ shows peaks at 0.78–1.07 ppm (t; 6H); 1.31–1.49 ppm (m; 4H); 1.48–1.59 ppm (m, 2H); 1.59–1.74 ppm (m; 2H); 1.75–1.99 ppm (m, 6H); 3.91–4.08 ppm (t; 4H); 4.22–4.37 ppm (t; 4H); 6.79–7.03 ppm (t, 2H); 7.14–7.29 ppm (t; 2H); 7.29–7.54 ppm (m; 14H); 7.71–7.85 ppm (s, 2H); 7.87–8.02 ppm (dd; 2H); 8.05–8.21 ppm (d; 2H); 8.25–8.43 ppm (d; 2H). This $^1$H-NMR spectrum is in agreement with the structure of Compound (8).

Compound (9)

Compound (9) was prepared according to the procedure of Compound (8) except that 1,5-dibromoheptane (0.05 mole) was replaced with 1,6-dibromohexane (0.05 mole, obtained from Aldrich Chemical Company). The melting point was found to be 186–187° C. The $^1$H-NMR spectrum of the final product in $CDCl_3$ shows peaks at 0.84–1.05 ppm (t; 6H); 1.32–1.48 ppm (m; 4H); 1.48–1.69 ppm (m; 4H); 1.73–1.99 ppm (m; 8H); 3.90–4.08 ppm (t; 4H); 4.21–4.40 ppm (t; 4H); 6.84–6.97 ppm (t; 2H); 7.15–7.25 ppm (t; 2H); 7.29–7.56 ppm (m; 14H); 7.71–7.84 ppm (s; 2H); 7.84–7.99 ppm (dd; 2H); 8.06–8.22 ppm (d; 2H); 8.26–8.43 ppm (d; 2H). The $^1$H-NMR spectrum is in full agreement with structure of Compound (9).

Compound (10)

Compound (10) was prepared according to the procedure of Compound (8) except that 1,5-dibromoheptane (0.05 mole) was replaced by 1,8-dibromooctane (0.05 mole, obtained from Aldrich Chemical Company). The $^1$H-NMR spectrum of the final product in $CDCl_3$ shows peaks at 0.80–1.09 ppm (t; 6H); 1.19–1.98 ppm (m; 20 H); 3.85–4.07 ppm (t; 4H); 4.17–4.40 ppm (t; 4H); 6.83–6.97 ppm (t; 2H); 7.13–7.56 ppm (m; 16 H); 7.69–7.83 ppm (s; 2H); 7.85–7.99 ppm (dd; 2H); 8.05–8.20 ppm (d; 2H); 8.25–8.41 ppm (d; 2H). The $^1$H-NMR spectrum is in agreement with the structure of Compound (10).

G. Ionization Potential Protocol

Samples for ionization potential (Ip) measurements were prepared by dissolving Examples 2, 3, 5, 6, 8, 9, and Comparative Example A independently in tetrahydrofuran. Each solution was hand-coated on an aluminized polyester substrate that was precision coated with a methylcellulose-based adhesion sub-layer to form a charge transfer material (CTM) layer. The role of this sub-layer was to improve adhesion of the CTM layer, to retard crystallization of CTM, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of both the sub-layer and CTM layer was ~0.4 μm. No binder material was used with CTM in the preparation of the samples for Ip measurements. In most cases, the thin CTM layers were in a meta-stabile amorphous phase, delaying crystallization for several hours, so that measurement of the sample was possible. In some cases, however, crystallization began immediately after coating, as was observed with Compound (9). The sample layer of this CTM was amorphous but crystal inclusions were present at the time of the Ip measurement.

The ionization potential was measured by the electron photoemission in air method similar to that described in "Ionization Potential of Organic Pigment Film by Atmospheric Photoelectron Emission Analysis", *Electrophotography*, 28, Nr. 4, p. 364. (1989) by E. Miyamoto, Y. Yamaguchi, and M. Yokoyama, which is hereby incorporated by reference. The samples were illuminated with monochromatic light from the quartz monochromator with a deuterium lamp source. The power of the incident light beam was $2-5 \cdot 10^{-8}$ W. The negative voltage of −300 V was supplied to the sample substrate. The counter-electrode with the 4.5×15 $mm^2$ slit for illumination was placed at 8 mm distance from the sample surface. The counter-electrode was connected to the input of the BK2-16 type electrometer, working in the open input regime, for the photocurrent measurement. A $10^{-15}$–$10^{-12}$ amp photocurrent was flowing in the circuit under illumination. The photocurrent, I, was strongly dependent on the incident light photon energy hv. The $I^{0.5}$=f(hv) dependence was plotted. Usually the dependence of the square root of photocurrent on incident light quanta energy is well described by linear relationship near the threshold [see references "Ionization Potential of Organic Pigment Film by Atmospheric Photoelectron Emission Analysis", *Electrophotography*, 28, Nr. 4, p. 364. (1989) by E. Miyamoto, Y. Yamaguchi, and M. Yokoyama; and "Photoemission in Solids", Topics in Applied Physics, 26, 1–103. (1978) by M. Cordona and L. Ley]. The linear part of this dependence was extrapolated to the hv axis and Ip value was determined as the photon energy at the interception point. The ionization potential measurement has an error of ±0.03 eV.

H. Hole Mobility

Samples for charge carrier mobility measurements were prepared by dissolving Examples 2, 3, 5, 6, 8, and Comparative Example A independently in tetrahydrofuran with a binder to form 10% solid solutions. The binder was polycarbonate Z 200 (commercially obtained from Mitsubishi Engineering Plastics, White Plains, N.Y.). The sample/binder ratio was 4:6 or 5:5. Each solution was coated on an aluminized polyester substrate to form a charge transfer material (CTM) layer. The thickness of the CTM layer varied in the range of 5–10 µm. The mobility for samples such as Compound (9) with limited solubility could not be measured.

The hole drift mobility was measured by a time of flight technique as described in "The discharge kinetics of negatively charged Se electrophotographic layers," Lithuanian Journal of Physics, 6, p. 569–576 (1966) by E. Montrimas, V. Gaidelis, and A. Pažera, which is hereby incorporated by reference. Positive corona charging created electric field inside the CTM layer. The charge carriers were generated at the layer surface by illumination with pulses of nitrogen laser (pulse duration was 2 ns, wavelength 337 nm). The layer surface potential decreased as a result of pulse illumination was up to 1–5% of initial potential before illumination. The capacitance probe that was connected to the wide frequency band electrometer measured the speed of the surface potential dU/dt. The transit time $t_t$ was determined by the change (kink) in the curve of the dU/dt transient in linear or double logarithmic scale. The drift mobility was calculated by the formula $\mu = d^2/U_0 \cdot t_t$, where d is the layer thickness and $U_0$ is the surface potential at the moment of illumination.

Mobility values at electric field strength, E, of $6.4 \cdot 10^5$ V/cm are given in the Table 3. The mobility field dependencies may be approximated by the function $$\mu \sim e^{\alpha \sqrt{E}}$$

where α is parameter characterizing mobility field dependence. The value of the parameter α is also given in Table 3.

TABLE 3

Hole mobility and ionization potential of charge transport materials

| Compound | Solubility | Mobility µ, cm²/V · s at 6.4 · 10⁵ V/cm | Mobility Relative to HCTM1 | α | Ip, eV |
|---|---|---|---|---|---|
| 2 | Sol. w/heat | 40:60 | | | 5.44 |
| 3 | Sol. w/heat | 1.1 × 10–5 at 40:60 with PC | 1.22 | | 5.34 |
| 5 | Sol. w/o heat | 1.7 × 10–5 at 40:60 with PC | 1.88 | ~0.006 | 5.38 |
| 6 | Sol. w/o heat | 6.5 × 10–6 at 40:60 with PC | 0.72 | 0.0053 | 5.23 |
| 8 | Sol. w/o heat | 3.6 × 10–6 at 40:60, 5.6 × 10–6 at 50:50 with PC | 0.40 0.62 | ~0.007 0.009 | 5.4 |
| 9 | Insoluble | | | | 5.35, layer with crystal inclusions |
| Comparative Example A* | | 5.2 · 10⁻⁶ at 40:60 with PC 9 · 10⁻⁶ at 50:50, | 0.58 1.00 | ~0.006 0.0055 | 5.23 |

*Comparative Example A was Compound (2) in U.S. Pat. No. 6,140,004, which is hereby incorporated by reference.

I. Extended Electrostatic Cycling

Extended electrostatic cycling was performed using an in-house designed and developed test bed that tests up to 3 samples strips that were wrapped around a drum. The three coated sample strips, each measuring 50 cm long by 8.8 cm wide, were fastened side-by-side and completely around an aluminum drum (50.3 cm circumference). At least one of the strips was a control sample (Comparative Example A) that was precision web coated and used as an internal reference point. In this electrostatic cycling tester, the drum rotated at a rate of 8.13 cm/s (3.2 ips) and the location of each station in the tester (distance and elapsed time per cycle) is given in Table 4:

TABLE 4

Electrostatic test stations around the sample sheet wrapped drum.

| Station | Degrees | Total Distance, cm | Total Time, sec |
|---|---|---|---|
| Front erase bar edge | 0° | Initial, 0 cm | Initial, 0 s |
| Erase Bar | 0–7.2° | 0–1.0 | 0–0.12 |
| Scorotron | 113.1–135.3° | 15.8–18.9 | 1.94–2.33 |
| Laser Strike | 161.0° | 22.5 | 2.77 |
| Probe #1 | 181.1° | 25.3 | 3.11 |
| Probe #2 | 251.2° | 35.1 | 4.32 |
| Erase bar | 360° | 50.3 | 6.19 |

The first electrostatic probe (Trek 344 electrostatic meter, commercially obtained from Trek Inc., Medina, N.Y.) is located 0.34 s after the laser strike station and 0.78 s after the scorotron. Also, the second probe (Trek 344 electrostatic meter) is located 1.21 s from the first probe and 1.99 s from the scorotron. All measurements were performed at ambient temperature and relative humidity.

Electrostatic measurements were obtained as a compilation of several tests. The first three diagnostic tests (prodtest initial, VlogE initial, dark decay initial) are designed to evaluate the electrostatic cycling of a new, fresh sample and the last three, identical diagnostic tests (prodtest final, VlogE final, dark decay final) are run after cycling of the sample (longrun).
1) PRODTEST: The erase bar was turned on during this diagnostic test and the sample recharged at the beginning of each cycle (except where indicated as scorotron off). The test sequence was as follows. The sample was completely charged for three complete drum revolutions (laser off); discharged with the laser @ 780 nm & 600 dpi on the forth cycle; completely charged for the next three cycles (laser off); discharged with only the erase lamp @ 720 nm on the eighth cycle (corona and laser off); and, finally, completely charged for the last three cycles (laser off).
2) VLOGE: This test measures the photoinduced discharge of the photoconductor to various laser intensity levels by monitoring the discharge voltage of the belt as a function of the laser power (exposure duration of 50 ns). The complete sample was charged and discharged at incremental laser power levels per each drum revolution. A semi-logarithmic plot was generated (voltage verses log E) to identify the sample's sensitivity and operational power settings.
3) DARK DECAY: This test measures the loss of charge acceptance with time without laser or erase illumination and can be used as an indicator of (i) the injection of residual holes from the charge generation layer to the charge transport layer, (ii) the thermal liberation of trapped charges, and (iii) the injection of charge from the surface or aluminum ground plane. After the belt has been completely charged, it was stopped and the probes measured the surface voltage over a period of 90 seconds. The decay in the initial voltage was plotted verses time.
4) LONGRUN: The belt was electrostatically cycled for 100 drum revolutions according to the following sequence per each belt-drum revolution. The belt was charged by the corona, the laser was cycled on and off (80–100° sections) to discharge a portion of the belt and, finally, the erase lamp discharged the whole belt in preparation for the next cycle. The laser was cycled so that the first section of the belt was never exposed, the second section was always exposed, the third section was never exposed, and the final section was always exposed. This pattern was repeated for a total of 100 drum revolutions and the data for every $5^{th}$ cycle was recorded.
5) After the 100th cycle (long run test), the PRODTEST, VLOGE, DARK DECAY diagnostic tests were run again.

Table 5 shows the results from the prodtest initial and prodtest final diagnostic tests. The values for the charge acceptance voltage (Vacc, probe #1 average voltage obtained from the third cycle), discharge voltage (Vdis, probe #1 average voltage obtained from the fourth cycle), functional dark decay voltage (Vdd, average voltage difference between probes 1 & 2 obtained from the third cycle), and the residual voltage (Vres, average voltage obtained from the eighth cycle) are reported for the initial and final (post $100^{th}$ cycle) cycles.

TABLE 5

Electrostatic cycling of knife-coated inverted dual layer constructions.

| Compound | Vacc, intl | Vacc, final | Vdd, intl | Vdd, final | Vdis, intl | Vdis, final | Vres, intl | Vres, final |
|---|---|---|---|---|---|---|---|---|
| 2 | 526 | 548 | 39 | 43 | 100 | 113 | 43 | 57 |
| 3 | 495 | 509 | 44 | 44 | 67 | 73 | 22 | 31 |
| 5 | 639 | 686 | 54 | 46 | 545 | 612 | 434 | 488 |
| 6 | 546 | 568 | 40 | 38 | 104 | 127 | 42 | 67 |
| 8 | 513 | 550 | 53 | 49 | 218 | 257 | 119 | 158 |
| 10 | 539 | 576 | 38 | 34 | 161 | 203 | 77 | 123 |
| Comparative Example A* | 568 | 577 | 32 | 36 | 57 | 62 | 16 | 23 |
| Comparative Example A* | 500 | 525 | 17 | 26 | 73 | 81 | 22 | 30 |

*Comparative Example A was performed with Compound 2 in U.S. Pat. No. 6,140,004.

A. Synthesis

Compound (13)

Compound (13) was synthesized as follows. To a 2-Liter 3-neck round bottom flask, equipped with mechanical stirrer and reflux condenser, were added 112.0 g (0.41 mole) of 4-(diphenylamino)benzaldehyde (commercially obtained from Aldrich, Milwaukee, Wis. and used as received) followed by the addition of 400 ml of THF. To this solution, were added, 48.77 g (0.45 mole) of phenylhydrazine (commercially obtained from Aldrich, Milwaukee, Wis. and used as received). The solution was refluxed for 2 hours. After cooled to room temperature, the solvent was evaporated from the solution till the volume of the solution was 50 ml. Then a solid was precipitated by the addition of ethanol (50 ml), collected by filtration, washed with ethanol (50 ml), and dried in oven vacuum for 6 hours at 60° C. The yield was 146 g (98%). The $^1$H-NMR spectrum and IR spectrum of the solid in $CDCl_3$ were in complete agreement with the expected product. The $^1$H-NMR spectrum of the solid shows peaks at 3.8 ppm (N—H) (s; 1H) and 7.19–7.55 ppm (m; 20H). The IR spectrum of the solid shows peaks at 1688 $cm^{-1}$ (C=O) and 3293 $cm^{-1}$ (N—H).

To a 250 ml 3-neck round bottom flask, equipped with mechanical stirrer and thermometer, were added DMSO (100 ml) and the solid product (18.17 g, 0.05 mole) from the reaction described above. The solution was heated at 30° C. until the solid product entered into solution. 1,5-Dibromopentane (5.75 g, 0.025 mole) (commercially obtained from Aldrich, Milwaukee, Wis.) was added to the solution and then 25% NaOH aqueous solution (20 g) was added. This solution was heated at 70–80° C. for 4 hours. After cooled to room temperature, a gummy material was observed in the bottom of the 3-neck round bottom flask. The liquid above the gummy material was removed by decantation. The remaining gummy material was washed repeatedly with water to form a solid which then was recrystallized first from toluene/ethanol (50:50 by volume) with activated charcoal. The material was recrystallized for the second and third time from ethanol with activated charcoal and silica gel (added only in the third recrystallization). The product was dried at 50° C. oven vacuum for 6 hours. The yield was 7.90 g (40%). The melting point was found to be 77° C. The $^1$H-NMR spectrum and the IR spectrum of the product in $CDCl_3$ were in complete agreement with the proposed structure of Compound (13). The $^1$H-NMR spectrum of the solid showed peaks at 1.51–1.59 ppm (m; 2H); 1.73–1.81 ppm (t; 4H); 3.86–3.99 ppm (t; 4H); and 6.95–7.64 ppm (m; 40H). The IR spectrum showed peaks at 2847 $cm^{-1}$, 2910 $cm^{-1}$, and 3031 $cm^{-1}$.

B. $^1$H-NMR Measurements

The $^1$H-NMR spectra were obtained by a 300 MHz Bruker NMR spectrometer (obtained commercially from Bruker Instruments Inc., Billerica, Mass.) using $CDCl_3$ solvent with 0.03% v/v tetramethylsialine (obtained commercially from Aldrich Chemical Company) as the internal reference. The following abbreviations were used: s=singlet; d=doublet; dd=double doublet; m=multiplet; q=quartet; and t=triplet.

C. IR Spectrum Measurements

The IR sample was obtained by placing a $CH_2Cl_2$ solution of the sample on an IR card (3M disposable substrate type 61 polyethylene obtained commercially from 3M, St. Paul, Minn.). The IR spectrum was obtained by a Perkin Elmer 16 PC FT-IR Spectrometer obtained commercially from Perkin Elmer, Norwalk, Conn.

D. Melting Point Measurement

Melting Point of Compound (13) was collected using a TA Instruments Model 2929 Differential Scanning Calorimeter (New Castle, Del.) equipped with a DSC refrigerated cooling system (−70° C. minimum temperature limit), and dry helium and nitrogen exchange gases. The calorimeter ran on a Thermal Analyst 2100 workstation with version 8.10B software. An empty aluminum pall was used as the reference.

The samples were prepared by placing 4.0 to 8.0 mg of Compound (13) into an aluminum sample pan and crimping the upper lid to produce a hermetically sealed sample for DSC testing. The results were normalized on a per mass basis.

Each sample was subjected to the following protocol to evaluate its thermal transition behavior:
17. Equilibrate at 0° C. (Default—Nitrogen Heat Exchange Gas);
18. Isothermal for 5 min.;
19. External Event: Nitrogen Heat Exchange Gas;
20. Ramp 10.0° C./min. to a temperature 200° C.;

E. Organophotoreceptor Preparation Method

Inverted dual layer organophotoreceptors were prepared incorporating Compound (13) and Comparative Example A (using Compound (2) in U.S. Pat. No. 6,140,004). A charge transport solution containing 50 wt. % of Compound (13) in Polycarbonate Z binder was prepared by combining a solution of 1.25 g of Compound (13) in 8.0 g of tetrahydrofuran with 1.25 g of Polycarbonate Z in 2.50 g of toluene. The charge transport solution was then hand-coated with a Meyer rod (# 40) onto a 76 micrometer (3 mil) thick aluminized polyethylene terephthalate film (Melinex®442 polyester film from Dupont having a 1 ohm/square aluminum vapor coat) having a 0.3 micron polyester resin sublayer (Vitel® PE-2200 from Bostik, Middletown, Mass.) and dried to form a charge transport layer having a thickness of 9 micrometers.

A dispersion was prepared by micronising 1.35 g of oxytitanium phthalocyanine pigment (H. W. Sands Corp., Jupiter, Fla.), 1.35 g of S-Lec B Bx-5 polyvinylbutryal resin (Sekisui Chemical Co. Ltd.), 26 g of methyl ethyl ketone, and 13 g of toluene using a horizontal sand mill operating in recirculation mode for 8 hours. The resulting dispersion was then die coated onto unsubbed 2 mil (51 micrometer) thick polyethylene terephthalate (PET) film and dried at 80° C. for 10 minutes to form a charge generating layer having a thickness of 0.27 micrometer on the PET film.

The charge transport layer and the charge generating layer were laminated together at 140° C. using a Model 447 Matchprint™ Laminator (obtained commercially from Imation Corp., Oakdale, Minn.). After lamination, the 2 mil (51 micrometer) PET film was peeled off the surface of the charge generation layer to form the inverted dual layer organophotoreceptor.

F. Electrostatic Testing

Electrostatic testing was performed on a number of inverted dual layer organophotoreceptor samples. The samples were prepared either by lamination or by die coating.

Electrostatic testing of Compound (13) and Comparative Example A (using Compound (2) in U.S. Pat. No. 6,140,004) was performed and recorded on a QEA PDT-2000 instrument at ambient temperature. Charge-up was performed at 8 kV. Discharge was performed by exposing the photoreceptor to a 780 nm-filtered tungsten light source down a fiber optic cable. Each sample was exposed to 2 microjoules/cm² of energy for 0.05 seconds; the total exposure intensity was 20 microwatts/cm². After charge-up, the acceptance voltage ($V_{acc}$) was measured in volts. This value was recorded as $V_{acc}$ after one cycle. Following this initial charge-up, a one second dark decay followed before the sample was discharged with the 0.05 second light pulse of 2 microjules/cm² at 780 nm, one second after which the decrease in voltage (Contrast) was measured in volts. Then the charge on the sample was further reduced by an eraser lamp. The final residual voltage ($V_{res}$) on the sample was measured in volts. $V_{acc}$ and $V_{res}$ were also measured after a total of 1000 cycles. In general, it is desirable to maximize $V_{acc}$ and to minimize $V_{res}$.

TABLE 6

| Sample | $V_{acc}$ (V) | Dark Decay (V) | $V_{res}$ (V) | Contrast (V) |
|---|---|---|---|---|
| Compound 13 | 363 | 142 | 18 | 195 |
| Comparative Example A | 377 | 135 | 16 | 211 |

The data in Table 6 indicate that Compound (13) is suitable for making photoreceptors.

Compound (14)

The first step is the preparation of a 3-formyl-9-ethylcarbazole by Vilsmeier reaction. 9-Ethylcarbazole (obtained commercially from Aldrich Chemical Company, Milwaukee, Wis.) is dissolved in dimethylformamide (DMF) and then the solution is cooled. Phosphorus oxychloride ($POCl_3$) (10–15% excess) is added slowly via a dropping funnel to the cooled DMF solution. 3-Formyl-9-ethylcarbazole is isolated and purified.

To a 2-liter 3-neck round bottom flask equipped with mechanical stirrer, reflux condenser and heating mantle, 3-formyl-9-ethylcarbazole (1 mole, 223 g) and tetrahydrofuran (600 ml) are added. Heat is applied to ensure that all solid enters into solution. Phenyl hydrazine (119 g, 1.1 mole, obtained commercially from Aldrich Chemical Company, Milwaukee, Wis.) is added and the mixture is refluxed for 2 hours. When thin layer chromatography (TLC) shows the total disappearance of the starting material and the formation of the product, the flask is allowed to cool to room temperature and the solvent is evaporated. 3-Formyl-9-ethylcarbazole hydrazone is isolated and purified.

To a 2-liter 3-neck round bottom flask equipped with mechanical stirrer, reflux condenser and heating mantle, 4-(diphenylamino)benzaldehyde (1 mole, 273 g, commercially obtained from Fluke, Milwaukee, Wis.) and tetrahydrofuran (600 ml) are added. Heat is applied to ensure that all solid enters into solution. Phenyl hydrazine (119 g, 1.1 mole, obtained commercially from Aldrich Chemical Company, Milwaukee, Wis.) is added and the mixture is refluxed for 2 hours. When TLC shows the total disappearance of the starting material and the formation of the product, the flask is allowed to cool to room temperature and the solvent is evaporated. 4-(Diphenylamino)benzaldehyde hydrazone is isolated and purified.

To a 2-liter 3-neck round bottom flask equipped with mechanical stirrer, reflux condenser and heating mantle, 4-quinolinecarboxaldehyde (1 mole, 157.17 g, obtained commercially from Aldrich Chemical Company, Milwaukee, Wis.) and tetrahydrofuran (600 ml) ) are added. Heat is applied to ensure that all solid enters into solution. Phenyl hydrazine (119 g, 1.1 mole, obtained commercially from Aldrich Chemical Company, Milwaukee, Wis.) is added and the mixture is refluxed for 2 hours. When TLC shows the total disappearance of the starting material and the formation of the product, the flask is allowed to cool to room temperature and the solvent is evaporated. 4-Quinolinecarboxaldehyde hydrazone is isolated and purified.

The last step is the reaction of 3-formyl-9-ethylcarbazole hydrazone, 4-(diphenylamino)benzaldehyde hydrazone, and 4-quinolinecarboxaldehyde hydrazone obtained above with a 1,2,3-tribromopropane to form Compound (14). 3-Formyl-9-ethylcarbazole hydrazone is dissolved in DMSO. After the addition of 25% aqueous solution of NaOH, 1,2,3-tribromopropane is added to the solution. The molar ratio of 3-formyl-9-ethylcarbazole hydrazone to 1,2,3-tribromopropane is 1:1. This solution is stirred at 70° C. for approximately 1 hour. To this solution, 4-(diphenylamino)-benzaldehyde hydrazone is added. The molar ratio of 4-(diphenylamino)benzaldehyde hydrazone to 1,2,3-tribromopropane is 1:1. After the addition is completed, the solution is heated at 70° C. for additional one hour. To this solution is added 4-quinolinecarboxaldehyde hydrazone. The molar ratio of 4-quinolinecarboxaldehyde hydrazone to 1,2,3-tribromopropane is 1:1. After the addition is completed, the solution is heated at 70° C. for additional one hour. The product from this reaction is isolated and purified. Compound (15)

The first step is the preparation of a 3-formyl-9-ethylcarbazole by Vilsmeier reaction. 9-Ethylcarbazole (obtained commercially from Aldrich Chemical Company, Milwaukee, Wis.) is dissolved in dimethylformamide (DMF) and then the solution is cooled. Phosphorus oxychloride (POCl$_3$) (10–15% excess) is added slowly via a dropping funnel to the cooled DMF solution. 3-Formyl-9-ethylcarbazole is isolated and purified.

To a 2-liter 3-neck round bottom flask equipped with mechanical stirrer, reflux condenser and heating mantle, 3-formyl-9-ethylcarbazole (1 mole, 223 g) and tetrahydrofuran (600 ml) are added. Heat is applied to ensure that all solid enters into solution. Phenyl hydrazine (119 g, 1.1 mole, obtained commercially from Aldrich Chemical Company, Milwaukee, Wis.) is added and the mixture is refluxed for 2 hours. When TLC shows the total disappearance of the starting material and the formation of the product, the flask is allowed to cool to room temperature and the solvent is evaporated. 3-Formyl-9-ethylcarbazole hydrazone is isolated and purified.

To a 2-liter 3-neck round bottom flask equipped with mechanical stirrer, reflux condenser and heating mantle, 4-(diphenylamino)benzaldehyde (1 mole, 273 g, commercially obtained from Fluke, Milwaukee, Wis.) and tetrahydrofuran (600 ml) are added. Heat is applied to ensure that all solid enters into solution. Phenyl hydrazine (119 g, 1.1 mole, obtained commercially from Aldrich Chemical Company, Milwaukee, Wis.) is added and the mixture is refluxed for 2 hours. When TLC shows the total disappearance of the starting material and the formation of the product, the flask is allowed to cool to room temperature and the solvent is evaporated. 4-(Diphenylamino)benzaldehyde hydrazone is isolated and purified.

To a 2-liter 3-neck round bottom flask equipped with mechanical stirrer, reflux condenser and heating mantle, 9-formyl-julolidine (1 mole, 201 g, obtained commercially from Aldrich Chemical Company, Milwaukee, Wis.) and tetrahydrofuran (600 ml) are added. Heat is applied to ensure that all solid enters into solution. Phenyl hydrazine (119 g, 1.1 mole, obtained commercially from Aldrich Chemical Company, Milwaukee, Wis.) is added and the mixture is refluxed for 2 hours. When TLC shows the total disappearance of the starting material and the formation of the product, the flask is allowed to cool to room temperature and the solvent is evaporated. 9-Formyl-julolidine hydrazone is isolated and purified.

The last step is the reaction of 3-formyl-9-ethylcarbazole hydrazone, 4-(diphenylamino)benzaldehyde hydrazone, and 9-formyl-julolidine hydrazone obtained above with a 1,2,3-tribromopropane to form Compound (15). 3-Formyl-9-ethylcarbazole hydrazone is dissolved in DMSO. After the addition of 25% aqueous solution of NaOH, 1,2,3-tribromopropane is added to the solution. The molar ratio of 3-formyl-9-ethylcarbazole hydrazone to 1,2,3-tribromopropane is 1:1. This solution is stirred at 70° C. for approximately 1 hour. To this solution, 4-(diphenylamino)-benzaldehyde hydrazone is added. The molar ratio of 4-(diphenylamino)benzaldehyde hydrazone to 1,2,3-tribromopropane is 1:1. After the addition is completed, the solution is heated at 70° C. for additional one hour. To this 9-formyl-julolidine hydrazone is added. The molar ratio of 9-formyl-julolidine hydrazone to 1,2,3-tribromopropane is 1:1. After the addition is completed, the solution is heated at 70° C. for additional one hour. The product from this reaction is isolated and purified.

Compound (16)

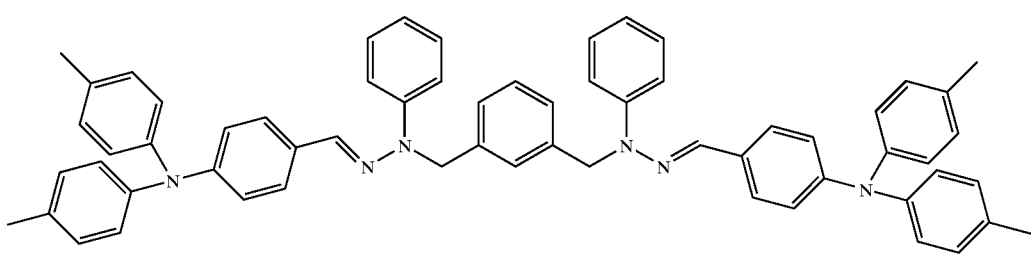

-continued
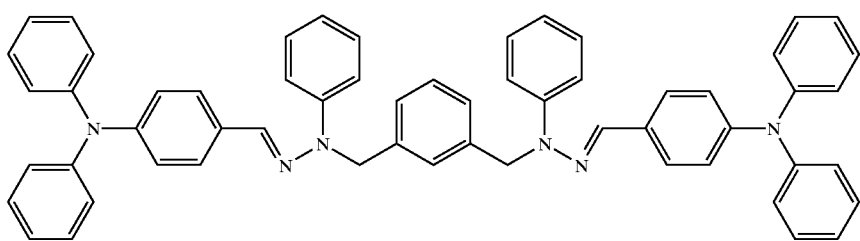
Compound (17)
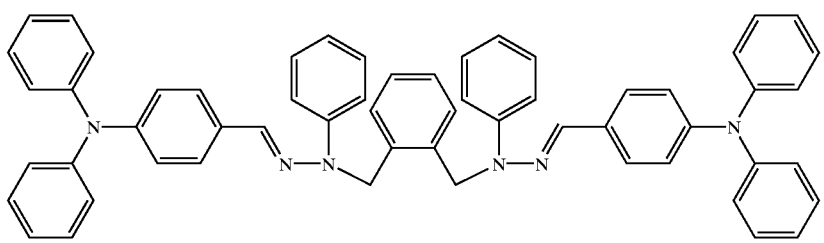
Compound (18)
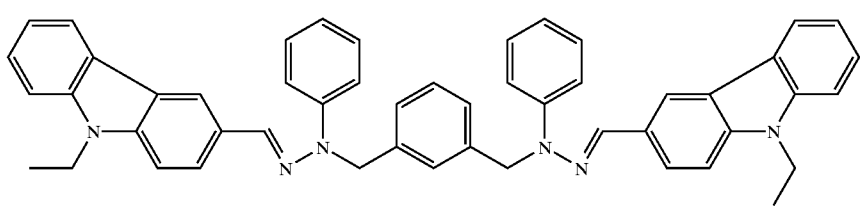
Compound (19)
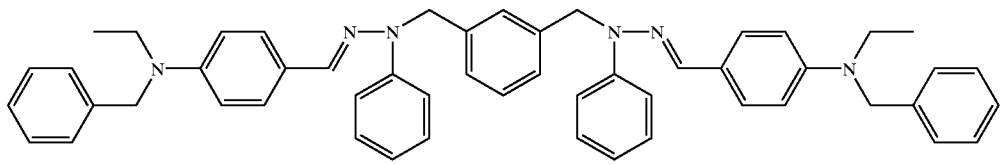
Compound (20)
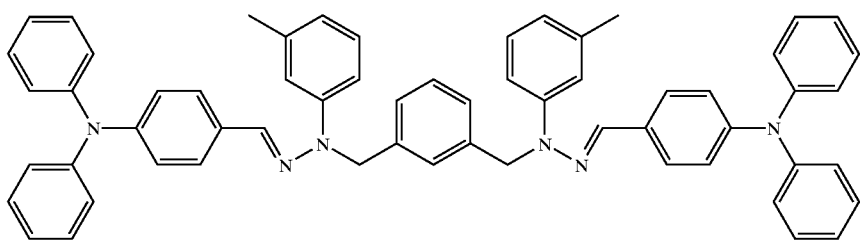
Compound (21)
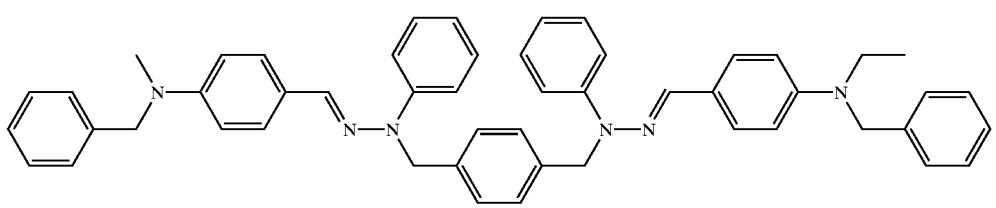
Compound (22)
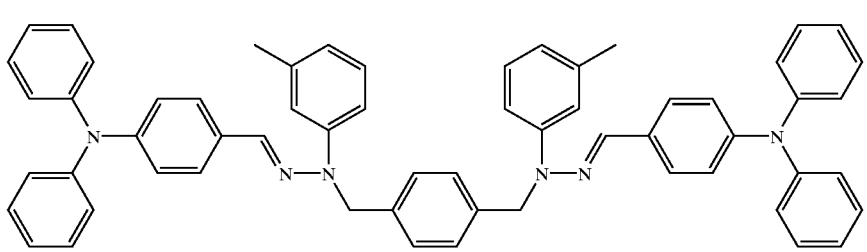
Compound (23)

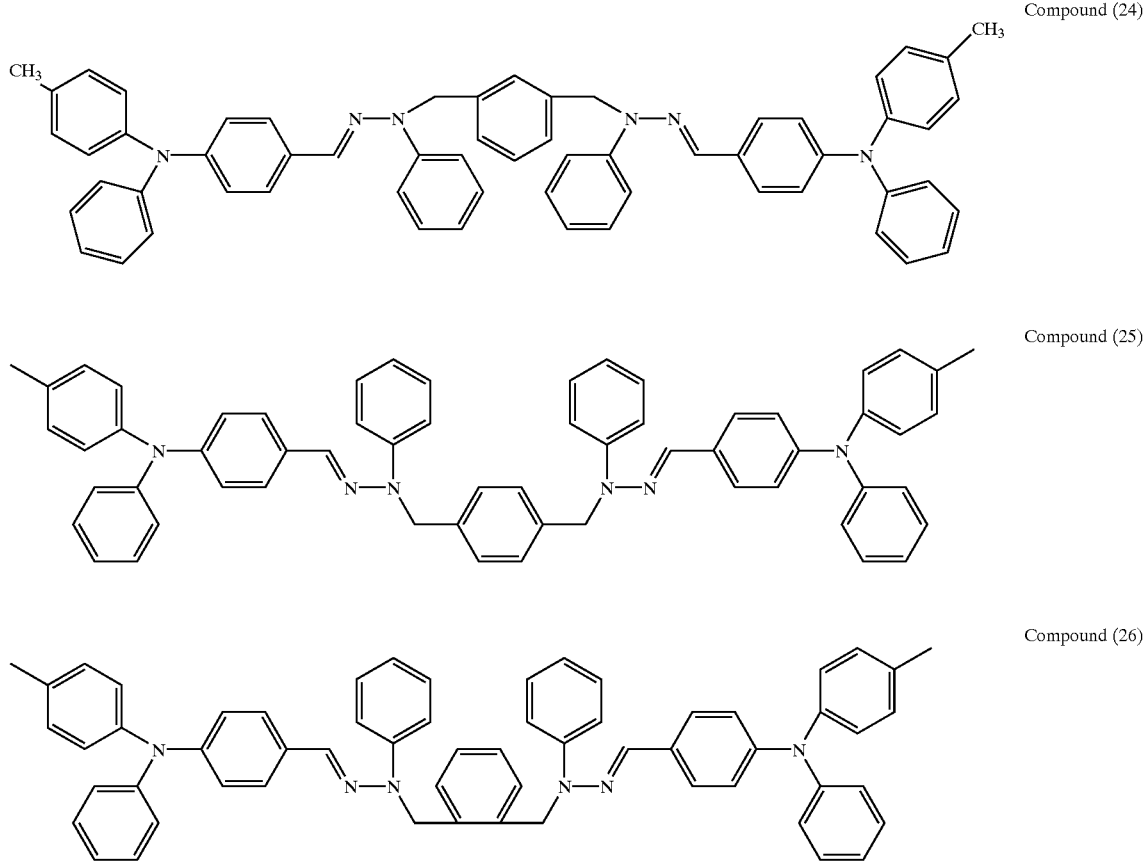

Compound (24)

Compound (25)

Compound (26)

A mixture of 4-(4,4'-dimethyldiphenylamino)benzaldehyde N-phenylhydrazone(3.9 g, 10.0 mmol) and α,α'-dibromo-1,3-dimethylbenzene (1.3 g, 5.0 mmol, obtained commercially from Aldrich Chemical Company, Milwaukee, Wis.) was dissolved in 30 ml of acetone and 0.1 g (0.27 mmol) of tetrabutylammonium iodide was added. The mixture was vigorously stirred at reflux for 1 hour, followed by the addition of 1.6 g of 85% powdered potassium hydroxide (KOH). The organic phase was separated and after evaporation of the solvent the residue was subjected by chromatography (silica gel, grade 62, 60–200 mesh, 150 Å, Aldrich) using 1:10 ethylacetate-hexane as the eluent. After removal of the eluents; the 20% solution of the oily residue in toluene was poured with intensive stirring into a tenfold excess of n-hexane. The yield was 3.35 g (77%). $^1$H-NMR spectrum (100 MHz, CDCl$_3$), ppm: 7.5–6.8 (m, 40H, Ar); 5.1 (s, 4H, 2×CH$_2$); 2.3 (s, 12H, 4×CH$_3$); Found, %: C83.99; H 6.19; N 9.32. C$_{62}$H$_{56}$N$_6$. Calculated, %: C 84.13; H 6.38; N 9.49.
Compound (17)

A mixture of 4-(diphenylamino)benzaldehyde N-phenylhydrazone (4.0 g 11.0 mmol) and α,α'-dibromo-1,3-dimethylbenzene (1.45 g 5.5 mmol, obtained commercially from Aldrich Chemical Company, Milwaukee, Wis.) was dissolved in 50 ml of butanone and 0.01 g (0.027 mmol) of tetrabutylammonium iodide was added. The mixture was vigorously stirred at reflux for 1 hour, followed by the addition of 1 g of 85% powdered KOH (15 mmol). The solid obtained was filtered and washed with acetone, twice with water and repeatedly with acetone. The yield was 3.4 g (75%); m.p. 132.5–134° C. (recrystallized from toluene). 1H-NMR spectrum (100 MHz, CDCl$_3$), ppm: 7.6–6.8 (m, 44H, Ar); 5.1 (s, 4H, CH$_2$). Found, %: C 83.88; H 5.73; N 10.0 8. C$_{58}$H$_{48}$N$_6$. Calculated, %: C 84.03; H 5.84; N 10.14.
Compound (18)

A mixture of 4-(diphenylamino)benzaldehyde N-phenylhydrazone (4.0 g 11.0 mmol) and α,α'-dibromo-1,2-dimethylbenzene (1.45 g 5.5 mmol, obtained commercially from Aldrich Chemical Company, Milwaukee, Wis.) was dissolved in 50 ml of butanone and 0.01 g (0.027 mmol) of tetrabutylammonium iodide was added. The mixture was vigorously stirred at reflux for 1 hour, followed by the addition of 1 g of 85% powdered KOH (15 mmol). The solid obtained was filtered and washed with acetone, twice with water and repeatedly with acetone. The yield was 3.0 g (66%); m.p. 241–243° C. (recrystallized from dioxane). $^1$H-NMR spectrum (100 MHz, CDCl$_3$), ppm: 7.7–6.8 (m, 44H, Ar); 5.2 (s, 4H, CH$_2$). Found, %: C 83.92; H 5.78; N 10.05. C$_{58}$H$_{48}$N$_6$. Calculated, %: C 84.03; H 5.84; N 10.14.
Compound (19)

A mixture of 9-ethylcarbazole-3-carbaldehyde N-phenylhydrazone (4.0 g 12.8 mmol) and α,α'-dibromo-1,3-dimethylbenzene (1.69 g 6.4 mmol, obtained commercially from Aldrich Chemical Company, Milwaukee, Wis.) was dissolved in 50 ml of butanone and 0.01 g (0.027 mmol) of tetrabutylammonium iodide was added. The mixture was vigorously stirred at reflux for 1 hour, followed by the addition of 1.0 g of 85% powdered KOH (15 mmol). The organic phase was separated and after evaporation of the solvent the residue was subjected by chromatography (silica gel, grade 62, 60–200 mesh, 150 Å, Aldrich) using 1:4 acetone:hexane as the eluent. Fractions containing the product were collected and evaporated to afford oily residue that was crystallized from dioxane. The yield was 3.1 g (80%); m.p. 163–164° C. (recrystallized from dioxane). $^1$H-NMR spectrum (250 MHz, DMSO-d$_6$), ppm: 8.24 (s, 2H, 4-H$_{Ht}$); 8.05 (d, J=7.8 Hz, 2H, 1-H$_{Ht}$); 7.72 (d, J=7.8 Hz, 2H, 2-H$_{Ht}$); 7.57 (s,2H, CH=N); 7.50–7.10 (m, 20H, Ar); 6.94 (t, J=7.0 Hz, 2H, 4-H$_{Ph}$); 5.17 (s, 4H, CH$_2$Ph); 4.22 (q, J=7.4 Hz, 4H, CH$_2$CH$_3$); 1.34 (t, J=7.2 Hz, 6H, CH$_3$). Found, %: C 82.22;H 5.98; N 11.45. C$_{50}$H$_{44}$N$_6$. Calculated, %: C 82.39; H 6.08; N 11.53.

Compound (20)

A mixture of 4-(benzylethylamino)benzaldehyde N-phenylhydra-zone (4.0 g 12.2 mmol) and α,α'-dibromo-1,3-dimethylbenzene (1.6 g 6.1 mmol, obtained commercially from Aldrich Chemical Company, Milwaukee, Wis.) was dissolved in 50 ml of butanone and 0.01 g (0.027 mmol) of tetrabutylammonium iodide was added. The mixture was vigorously stirred at reflux for 1 hour, followed by the addition of 1.2 g of 85% powdered KOH (18 mmol). The organic phase was separated and after evaporation of the solvent the residue was subjected by chromatography (silica gel, grade 62, 60–200 mesh, 150 Å, Aldrich) using 1:10 ethylacetate:hexane as the eluent. Fractions containing the product were collected and evaporated. The 20% solution of the oily residue in toluene was poured with intensive stirring into a tenfold excess of n-hexane. The yield was 3.2 g (69%). $^1$H-NMR spectrum (100 MHz, CDCl$_3$), ppm: 7.6–6.5 (m, 34H, Ar); 5.1 (s, 4H, NNCH$_2$Ph); 4.5 (s, 4H, CH$_2$Ph); 3.5 (q, 4H, CH$_2$CH$_3$); 1.2 (t, 6H, CH$_3$). Found, %: C 81.96; H 6.80; N 10.95. C$_{52}$H$_{52}$N$_6$ Calculated, %: C 82.07; H 6.89; N 11.04.

Compound (21)

A mixture of 4-(diphenylamino)benzaldehyde N-(3-methylphenyl)-hydrazone (4.0 g 10.6 mmol) and α,α'-dibromo-1,3-dimethylbenzene (1.36 g 5.2 mmol, obtained commercially from Aldrich Chemical Company, Milwaukee, Wis.) was dissolved in 50 ml of butanone and 0.01 g (0.027 mmol) of tetrabutylammonium iodide was added. The mixture was vigorously stirred at reflux for 1 hour, followed by the addition of 1 g of 85% powdered KOH (15 mmol). The organic phase was separated and after evaporation of the solvent the residue was subjected by chromatography (silica gel, grade 62, 60–200 mesh, 150 Å, Aldrich) using 1:10 ethylacetate:hexane as the eluent. Fractions containing the product were collected and evaporated to afford oily residue that was crystallized from acetone. The yield was 2.9 g (65%); m.p. 172–173° C. (recrystallized from acetone). $^1$H-NMR spectrum (100 MHz, CDCl$_3$, ppm: 7.6–6.6 (m, 42H, Ar); 5.1 (s, 4H, CH$_2$); 2.3 (s, 6H, CH$_3$). Found, %: C 83.98; H 6.03; N 9.78. C$_{60}$H$_{52}$N$_6$. Calculated, %: C 84.08; H 6.12; N 9.81.

Compound (22)

4-(benzylethylamino)benzaldehyde N-phenylhydra-zone (4.0 g 12.2 mmol) and α,α'-dibromo-1,4-dimethylbenzene (1.6 g 6.1 mmol, obtained commercially from Aldrich Chemical Company, Milwaukee, Wis.) was dissolved in 50 ml of butanone and 0.01 g (0.027 mmol) of tetrabutylammonium iodide was added. The mixture was vigorously stirred at reflux for 1 hour, followed by the addition of 1.0 g of 85% powdered KOH (15 mmol). The organic phase was separated and after evaporation of the solvent the residue was subjected by chromatography (silica gel grade 62, 60–200 mesh, 150 Å, Aldrich) using 1:10 ethylacetate:hexane as the eluent. Fractions containing the product were collected and evaporated to afford oily residue that was crystallized from dioxane. The yield was 3.7 g (80%); m.p. 207–208.5° C. (recrystallized from dioxane). $^1$H NMR spectrum (100 MHz, CDCl$_3$), ppm: 7.6–6.5 (m, 34H, Ar); 5.1 (s, 4H, NNCH$_2$Ph); 4.5 (s, 4H, CH$_2$Ph); 3.5 (q, 4H, CH$_2$CH$_3$); 1.2 (t, 6H, CH$_3$). Found, %: C 81.96; H 6.80; N 10.95. C$_{52}$H$_{52}$N$_6$. Calculated, %: C 82.07; H 6.89; N 11.04.

Compound (23)

A mixture of 4-diphenylaminobenzaldehyde N-(3-methylphenyl)-hydrazone (4.0 g 10.6 mmol) and α,α'-dibromo-1,4-dimethylbenzene (1.36 g 5.2 mmol, obtained commercially from Aldrich Chemical Company, Milwaukee, Wis.) was dissolved in 50 ml of butanone and 0.01 g (0.027 mmol) of tetrabutylammonium iodide was added. The mixture was vigorously stirred at reflux for 1 hour, followed by the addition of 1 g of 85% powdered KOH (15 mmol). After removal of eluent hydrazone the oily residue was crystallized from acetone, washed twice with water and dried in vacuum. The yield was 3.7 g (83%); m.p. 245.5–247° C. $^1$H-NMR spectrum (100 MHz, CDCl$_3$), ppm: 7.6–6.6 (m, 42H, Ar); 5.1 (s, 4H, CH$_2$); 3.7 (s, 6H, CH$_3$). Found, %: C 83.98; H 6.03; N 9.78. C$_{60}$H$_{52}$N$_6$. Calculated, %: C 84.08; H 6.12; N 9.81.

Compound (24)

A mixture of 4-(4-methyldiphenylamino)benzaldehyde N-phenyl-hydrazone (4.0 g 10.6 mmol) and α,α'-dibromo-1,3-dimethylbenzene (1.36 g 5.2 mmol, obtained commercially from Aldrich Chemical Company, Milwaukee, Wis.) was dissolved in 50 ml of butanone and 0.01 g (0.027 mmol) of tetrabutylamonium iodide was added. The mixture was vigorously stirred at reflux for 1 hour, followed by the addition of 1 g of 85% powdered KOH (15 mmol). The organic phase was separated and after evaporation of the solvent the residue was subjected by chromatography (silica gel, grade 62, 60–200 mesh, 150 Å, Aldrich) using 1:10 ethylacetate:hexane as the eluent. The yield was 2.84 g (65%); m.p. 131–133° C. (recrystallized from acetone). $^1$H-NMR spectrum (100 MHz, CDCl$_3$), ppm: 7.6–6.7 (m, 42H, Ar); 5.1 (s, 4H, CH$_2$); 2.3 (s, 6H, CH$_3$). Found, %: C 83.99; H 6.09; N 9.72. C$_{60}$H$_{52}$N$_6$. Calculated, %: C 84.08; H 6.12; N 9.81.

Compound (25)

A mixture of 4-(4-methyldiphenylamino)benzaldehyde N-phenylhy-drazone (4.86 g 12.9 mmol) and α,α'-dibromo-1,4-dimethylbenzene (1.7 g 6.44 mmol, obtained commercially from Aldrich Chemical Company, Milwaukee, Wis.) was dissolved in 50 ml of butanone and 0.01 g (0.027 mmol) of tetrabutylammonium iodide was added. The mixture was vigorously stirred at reflux for 1 hour, followed by the addition of 1.2 g of 85% powdered KOH (18 mmol). The organic phase was separated and after evaporation of the solvent the oily residue was crystallized from acetone, washed twice with water and dried in vacuum. The yield was 4.0 g (72%). $^1$H-NMR spectrum (100 MHz, CDCl$_3$), ppm: 7.7–6.7 (m, 42H, Ar); 5.1 (s, 4H, CH$_2$); 2.3 (s, 6H, CH$_3$).

Found, %: C 83.96; H 6.07; N 9.69. $C_{60}H_{52}N_6$. Calculated, %: C 84.08; H 6.12; N 9.81.

Compound (26)

A mixture of 4-(4-methyldiphenylamino)benzaldehyde N-phenyl-hydrazone (4.0 g 10.6 mmol) and α,α'-dibromo-1,2-dimethylbenzene (1.36 g 5.2 mmol, obtained commercially from Aldrich Chemical Company, Milwaukee, Wis.) was dissolved in 50 ml of butanone and 0.01 g (0.027 mmol) of tetrabutylamonium iodide was added. The mixture was vigorously stirred at reflux for 1 hour, followed by the addition of 1 g of 85% powdered KOH (15 mmol). The organic phase was separated and after evaporation of the solvent the residue was subjected by chromatography (silica gel, grade 62, 60–200 mesh, 150 Å, Aldrich) using 1:10 ethylacetate:hexane as the eluent. Fractions containing the product were collected and evaporated to afford oily residue that was crystallized from acetone. The yield was 3.3 g (74%); m.p. 224.5–226.5° C. (recrystallized from acetone). $^1$H-NMR spectrum (100 MHz, $CDCl_3$), ppm: 7.7–6.7 (m, 42H, Ar); 5.1 (s, 4H, $CH_2$); 2.3 (s, 6H, $CH_3$). Found, %: C 83.99; H 6.05; N 9.79. $C_{60}H_{52}N_6$. Calculated, %: C 84.08; H 6.12; N 9.81.

Ionization Potential

The measurements of the ionization potential for Compounds 16, 19, 20, 21, 24, 25, and 26 are provided below.

Samples for ionization potential (Ip) measurements were prepared by dissolving the compound in tetrahydrofuran. The solution was hand-coated on an aluminized polyester substrate that was precision coated with a methylcellulose-based adhesion sub-layer to form a charge transport material (CTM) layer. The role of this sub-layer was to improve adhesion of the CTM layer, to retard crystallization of CTM, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of both the sub-layer and CTM layer was ~0.4 μm. No binder material was used with CTM in the preparation of the samples for Ip measurements.

The ionization potential was measured by the electron photoemission in air method similar to that described in "Ionization Potential of Organic Pigment Film by Atmospheric Photoelectron Emission Analysis", Electrophotography, 28, Nr. 4, p. 364. (1989) by E. Miyamoto, Y. Yamaguchi, and M. Yokoyama, which is hereby incorporated by reference. The samples were illuminated with monochromatic light from a quartz monochromator with a deuterium lamp source. The power of the incident light beam was $2-5 \cdot 10^{-8}$ W. The negative voltage of −300 V was supplied to the sample substrate. The counter-electrode with the 4.5×15 $mm^2$ slit for illumination was placed at 8 mm distance from the sample surface. The counter-electrode was connected to the input of the BK2-16 type electrometer, working in the open impute regime, for the photocurrent measurement. A $10^{-15}-10^{-12}$ amp photocurrent was flowing in the circuit under illumination. The photocurrent, I, was strongly dependent on the incident light photon energy hv. The $I^{0.5}$=f(hv) dependence was plotted. Usually the dependence of the square root of photocurrent on incident light quanta energy is well described by linear relationship near the threshold [see references "Ionization Potential of Organic Pigment Film by Atmospheric Photo-electron Emission Analysis", Electrophotography, 28, Nr. 4, p. 364. (1989) by E. Miyamoto, Y. Yamaguchi, and M. Yokoyama; and "Photoemission in Solids", Topics in Applied Physics, 26, 1–103. (1978) by M. Cordona and L. Ley, incorporated herein by reference]. The linear part of this dependence was extrapolated to the hv axis and Ip value was determined as the photon energy at the interception point. The ionization potential measurement has an error of ±0.03 eV.

The ionization potential data for Compounds 16, 19, 20, 21, 24, 25, and 26 are listed in Table 7.

TABLE 7

| Compound | $\mu_0$ ($cm^2/V \cdot s$) | $\mu$ ($cm^2/V \cdot s$) at $6.4 \times 10^5$ V/cm | α, $(cm/V)^{1/2}$ | Ionization Potential (eV) |
|---|---|---|---|---|
| 16 | $1.5 \cdot 10^{-6}$ | $4.0 \cdot 10^{-5}$ | 0.0041 | 5.28 |
| 19 | $5.8 \cdot 10^{-8}$ | $2.9 \cdot 10^{-6}$ | 0.0049 | 5.35 |
| 20 | $9.6 \cdot 10^{-8}$ | $3.8 \cdot 10^{-6}$ | 0.0046 | 5.07 |
| 21 | $2.4 \cdot 10^{-6}$ | $4.0 \cdot 10^{-5}$ | 0.0035 | 5.41 |
| 24 | $8 \cdot 10^{-7}$ | $2.2 \cdot 10^{-5}$ | 0.0042 | 5.35 |
| 25 | $4 \cdot 10^{-7}$ | $2 \cdot 10^{-5}$ | 0.0048 | 5.33 |
| 26 | $2.3 \cdot 10^{-6}$ | $3.3 \cdot 10^{-5}$ | 0.0033 | 5.33 |

Hole Mobility

The hole mobility measurements for Compounds 16, 19, 20, 21, 24, 25, and 26 are provided below.

The hole drift mobility was measured by a time of flight technique as described in "The discharge kinetics of negatively charged Se electrophotographic layers," Lithuanian Journal of Physics, 6, p. 569–576 (1966) by E. Montrimas, V. Gaidelis, and A. Pažera, which is hereby incorporated by reference. Positive corona charging created electric field inside the CTM layer. The charge carriers were generated at the layer surface by illumination with pulses of nitrogen laser (pulse duration was 2 ns, wavelength 337 nm). The layer surface potential decreased as a result of pulse illumination by up to 1–5% of initial pre-illumination potential. The capacitance probe that was connected to the wide frequency band electrometer measured the speed of the surface potential dU/dt. The transit time $t_t$ was determined by the change (kink) in the curve of the dU/dt transient in linear or double logarithmic scale. The drift mobility was calculated by the formula $\mu=d^2/U_0 \cdot t_t$, where d is the layer thickness and $U_0$ is the surface potential at the moment of illumination.

To prepare the sample for the measurements, a mixture of 0.1 g of the charge transport compound and 0.1 g of polycarbonate Z 200 (S-LEC B BX-1, commercially obtained from Sekisui) was dissolved in 2 ml of THF. The solution was coated on the polyester film with conductive Al layer by the dip roller method. After drying for 1 hour at 80° C., a clear 10 μm thick layer was formed. Samples were prepared for Compounds 16, 19, 20, 21, 24, 25, and 26. The hole mobility of the sample was measured and the results are presented in Table 7. Mobility values at electric field strength, E, of $6.4 \cdot 10^5$ V/cm are given in the Table 7 along with zero field mobilities $\mu_0$. The mobility field dependencies may be approximated by the function $$\mu \sim e^{\alpha\sqrt{E}}$$

where α is parameter characterizing mobility field dependence. The value of the parameter α is also given in Table 7.

The above descriptions and examples are intended to provide a broad and generic teaching and enablement of a generic invention. The examples should not be read as imposing limits upon the general and generic terms used to describe the practice of the present invention. Generic and specific embodiments are described within the following claims.

What is claimed is:

1. A charge transport compound having the following generic formula:

(R—Q)i n-Y wherein R is an (N,N-disubstituted)arylamine group

Q comprises an aromatic hydrazone linking group;

Y comprises a bridging group between R—Q— groups where Y comprises an aryl group or a heterocyclic group; and n is an integer between 2 and 6.

2. The charge transport compound of claim 1 wherein Q comprises an aromatic hydrazone linking group of the formula:

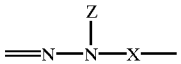

Z is an aryl group; and

X is a linking group.

3. The charge transport compound of claim 2 wherein R is a triphenylamine group.

4. The charge transport compound of claim 3 wherein Y comprises an aryl group.

5. The charge transport compound of claim 2 having the following formula

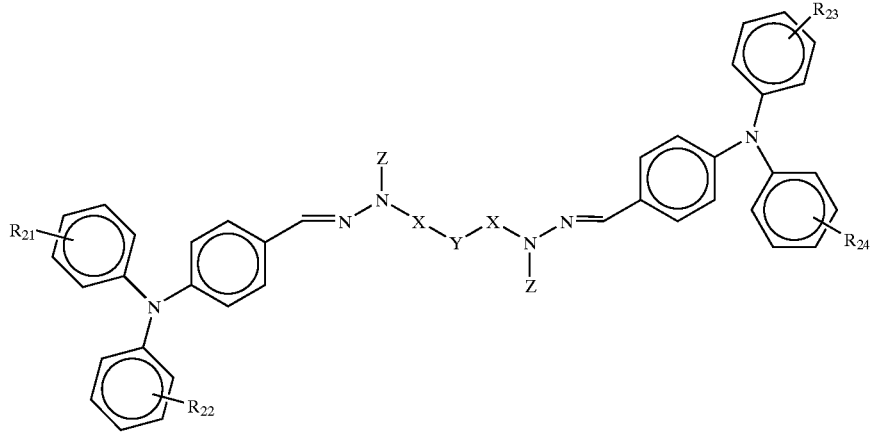

where $R_{21}$, $R_{22}$, $R_{23}$, and $R_{24}$ are, independently an alkyl group, an alkaryl group or an aryl group.

6. The charge transport compound of claim 5 wherein Y is an aryl group or a heterocyclic group, Z is an aryl group, and X is a bond or a methylene group.

7. The charge transport compound of claim 1 wherein R is a triarylamine group.

8. The charge transport compound of claim 7 wherein Y comprises an aryl group.

9. The charge transport compound of claim 1 wherein Q comprises an aromatic linking group of the formula:

C(R')=N—N—X, wherein R' is selected from the group consisting of hydrogen, alkyl groups, aryl groups, and alkaryl groups; and X is a linking group.

10. The charge transport compound of claim 9 wherein X is a methylene group.

11. An organic photoreceptor that includes:

(a) a charge transport compound having the formula (R—Q)n-Y wherein R is an (N,N-disubstituted)arylamine group;

Q comprises an aromatic hydrazone linking group;

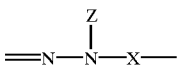

Y comprises a bridging group between R—Q— groups where Y comprises an aryl group or a heterocyclic group; and n is an integer between 2 and 6, inclusive;

(b) a charge generating compound; and (c) an electrically conductive substrate.

12. The organic photoreceptor of claim 11 wherein the aromatic hydrazone group has the formula:

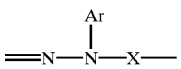

wherein Ar is an aromatic group, and

X is a divalent linking group selected from a chemical bond, carbon atom, nitrogen atom, oxygen atom, sulfur atom, a branched or linear —$(CH_2)_m$— group where m is an integer between 0 and 20, an aryl group, a cycloalkyl group, a cyclosiloxyl group, a heterocyclic group, and a $CR_{10}$ group where $R_{10}$ is hydrogen atom, an alkyl group, or aryl group.

13. The organic photoreceptor of claim 11 wherein the aromatic hydrazone group has the formula:

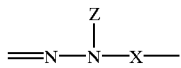

Z is a phenyl group; and

X is a methylene group.

14. An organic photoreceptor comprising:

(a) a charge transport compound having the formula

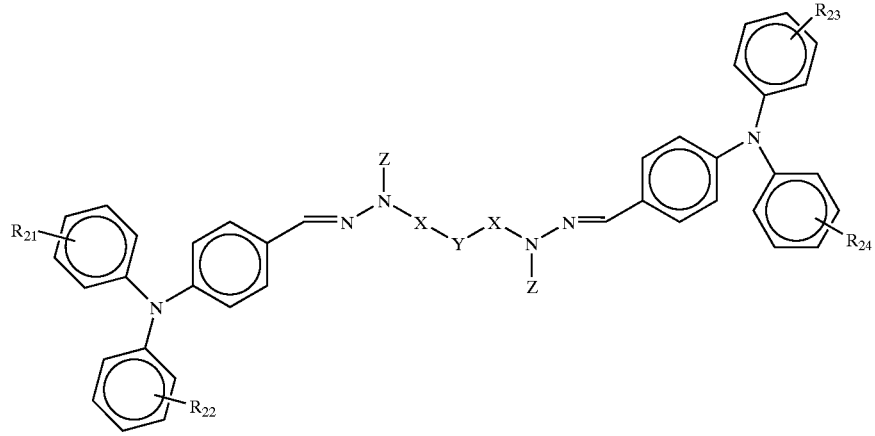

where $R_{21}$, $R_{22}$, $R_{23}$, and $R_{24}$ are, independently an alkyl group, an alkaryl group or an aryl group;

(b) a charge generating compound; and (c) an electrically conductive substrate.

15. An organic photoreceptor according to claim 14 wherein Y is an aryl group or a heterocyclic group, Z is an aryl group, and X is a bond or a methylene group.

16. An organic photoreceptor according to claim 14 comprising:

(a) a charge transport layer comprising said charge transport compound and a polymeric binder;

(b) a charge generating layer comprising said charge generating compound and a polymeric binder; and (c) said electrically conductive substrate.

17. An organic photoreceptor according to claim 14 wherein Y is an aryl group, Z is an aryl group, and X is a methylene group.

18. An electrophotographic imaging apparatus comprising:

(a) a plurality of support rollers, at least one having a diameter no greater than about 40 mm; and (b) an organic photoreceptor in the form of a flexible belt threaded around said support rollers, said organic photoreceptor comprising:

(i) a charge transport compound having the formula

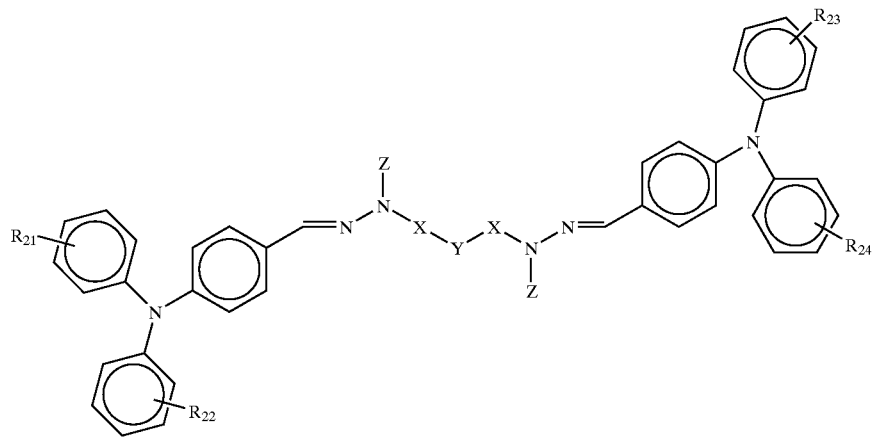

where $R_{21}$, $R_{22}$, $R_{23}$, and $R_{24}$ are, independently an alkyl group, alkaryl group or aryl group; Y is an aryl group or a heterocyclic group, Z is an aryl group, and X is a bond or a methylene group;

(ii) a charge generating compound; and (iii) an electrically conductive substrate.

19. An electrophotographic imaging apparatus according to claim 18 wherein Y is an aryl group, Z is an aryl group, and X is a methylene group.

20. An electrophotographic imaging process comprising:

(a) applying an electrical charge to a surface of an organic photoreceptor comprising:

(i) a charge transport compound having the formula

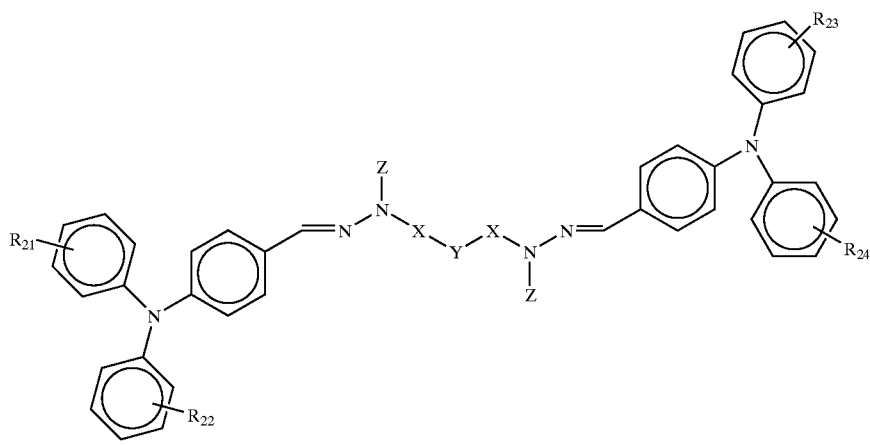

where $R_{21}$, $R_{22}$, $R_{23}$, and $R_{24}$ are, independently an alkyl group, an alkaryl group or an aryl group; Y is an aryl group or a heterocyclic group, Z is an aryl group, and X is a bond or a methylene group;

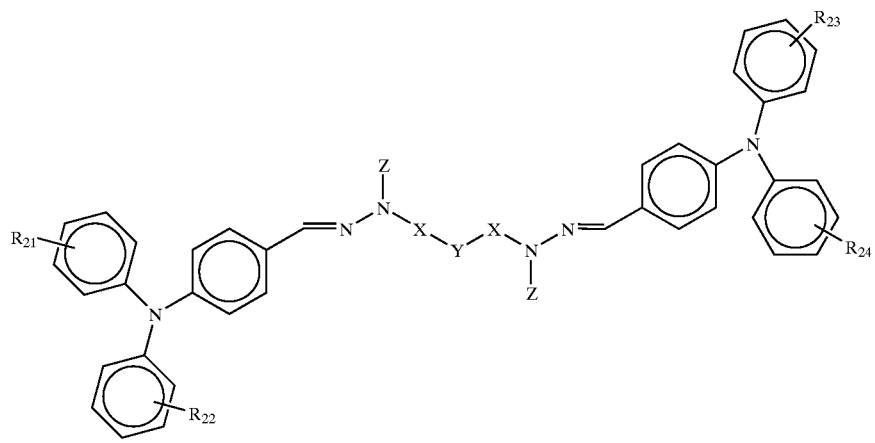

(ii) a charge generating compound; and (iii) an electrically conductive substrate;

(b) imagewise exposing said surface of said organic photoreceptor to radiation to dissipate charge in selected areas and thereby form a pattern of charged and uncharged areas on said surface;

(c) contacting said surface with a liquid toner comprising a dispersion of colorant particles in an organic liquid to create a toned image; and (d) transferring said toned image to a substrate.

21. An electrophotographic imaging process according to claim 20 wherein Y is an aryl group, Z is an aryl group, and X is a methylene group.

22. A charge transport compound having the formula where $R_{21}$, $R_{22}$, $R_{23}$, and $R_{24}$ are, independently an alkyl group, an alkaryl group or an aryl group; Y is an aryl group or a heterocyclic group, Z is an aryl group, and X is a bond or a methylene group.

* * * * *